United States Patent
Kim et al.

(10) Patent No.: US 7,842,199 B2
(45) Date of Patent: Nov. 30, 2010

(54) PROTON CONDUCTING TITANATE, POLYMER NANO-COMPOSITE MEMBRANE INCLUDING THE SAME, AND FUEL CELL ADOPTING THE POLYMER NANO-COMPOSITE MEMBRANE

(75) Inventors: Hae-kyoung Kim, Seoul (KR); Jae-sung Lee, Pohang-si (KR); Young-kwon Kim, Pohang-si (KR); Hyuk Chang, Seongnam-si (KR)

(73) Assignee: Samsung SDI Co., Ltd., Yongin-si (KR)

( * ) Notice: Subject to any disclaimer, the term of this patent is extended or adjusted under 35 U.S.C. 154(b) by 859 days.

(21) Appl. No.: 11/438,229

(22) Filed: May 23, 2006

(65) Prior Publication Data

US 2007/0053826 A1 Mar. 8, 2007

(30) Foreign Application Priority Data

May 25, 2005 (KR) .................. 10-2005-0044253

(51) Int. Cl.
*H01B 1/08* (2006.01)
*H01B 1/12* (2006.01)

(52) U.S. Cl. .............................. 252/519.12; 252/519.3; 252/519.31; 252/518.33; 252/519.4; 252/520.22; 429/40; 423/608

(58) Field of Classification Search ............ 252/519.12, 252/519.3, 519.31, 518.33, 519.4, 520.22; 429/40; 423/608
See application file for complete search history.

(56) References Cited

U.S. PATENT DOCUMENTS

| | | | | |
|---|---|---|---|---|
| 6,059,943 | A * | 5/2000 | Murphy et al. | 204/296 |
| 6,510,047 | B2 * | 1/2003 | Meiners et al. | 361/676 |
| 2006/0083962 | A1 * | 4/2006 | Takekawa et al. | 429/13 |
| 2006/0178500 | A1 * | 8/2006 | Kikuchi | 528/425 |
| 2006/0251965 | A1 * | 11/2006 | Nagayama et al. | 429/209 |
| 2006/0269816 | A1 * | 11/2006 | Kim et al. | 429/33 |
| 2007/0092776 | A1 * | 4/2007 | Akiyama et al. | 429/33 |
| 2008/0286628 | A1 * | 11/2008 | Briehn et al. | 429/33 |

FOREIGN PATENT DOCUMENTS

| | | |
|---|---|---|
| JP | 2003-282095 | 3/2003 |
| JP | 2005-79099 | 3/2005 |
| JP | 2006-291065 | 10/2006 |
| JP | 2006-327932 | 12/2006 |
| WO | WO 03/102971 | 12/2003 |
| WO | WO 2005013400 A2 * | 2/2005 |
| WO | WO 2005049183 A1 * | 6/2005 |
| WO | WO 2006/028190 | 3/2006 |
| WO | WO 2007048691 A2 * | 5/2007 |

OTHER PUBLICATIONS

Rhee et al., "Nanocomposite membranes of surface-sulfonated titanate and NAFLON (TM) for direct methanol fuel cells", Journal of Power Sources, 159 (2006), 1015-1024.*
Reg. No. 99601-82-8, Jan. 4, 1986.*
Reg. No. 1120-71-4, Nov. 16, 1984.*
Fuel Cell Scientific, LLC, Nafion—Fuel Cell Scientific, 2001, pp. 1 and 2.*
Rhee et al., "Template-free Hydrothermal Synthesis of High Surface Area Nitrogen-doped Titania Photocatalyst Active under Visible Light", Chemistry Letters, 34, 5 (Apr. 2, 2005), 660-661.*
Japanese Office Action issued Mar. 30, 2010, in corresponding Japanese Patent Application No. 2006-145956.

* cited by examiner

*Primary Examiner*—Douglas Mc Ginty
(74) *Attorney, Agent, or Firm*—Christie, Parker & Hale, LLP

(57) ABSTRACT

A proton conducting titanate includes titanate and a sulfonic acid group-containing moiety having proton conductivity introduced into the surface of the titanate, in which the sulfonic acid group-containing moiety is directly bound to the titanate via an ether bond (—O). A polymer nano-composite membrane includes the proton conducting titanate, and a fuel cell includes the polymer nano-composite membrane. The proton conducting titanate is provided with a sulfonic acid functional group having proton conductivity, which increases the proton conductivity of the polymer nano-composite membrane. The polymer nano-composite membrane includes the proton conducting titanate, and thus can have a controllable degree of swelling in a methanol solution, and the transmittance of the polymer nano-composite membrane can be reduced. The polymer nano-composite membrane can be used as a proton conducting membrane in fuel cells to improve the thermal stability, energy density, and fuel efficiency of the fuel cells.

25 Claims, 13 Drawing Sheets

PROTON CONDUCTING TITANATE, POLYMER NANO-COMPOSITE MEMBRANE INCLUDING THE SAME, AND FUEL CELL ADOPTING THE POLYMER NANO-COMPOSITE MEMBRANE

CROSS-REFERENCE TO RELATED APPLICATION

This application claims the benefit of Korean Patent Application No. 2005-44253, filed on May 25, 2005, in the Korean Intellectual Property Office, the disclosure of which is incorporated herein in its entirety by reference.

BACKGROUND OF THE INVENTION

1. Field of the Invention

Aspects of the present invention relate to a proton conducting titanate, a polymer nano-composite membrane including the same, and a fuel cell adopting the polymer nano-composite membrane, and more particularly, to a proton conducting titanate, a polymer nano-composite membrane including the proton conducting titanate and having reduced permeability to water and methanol and improved thermal stability, and a fuel cell having improved energy density and fuel efficiency by adopting the polymer nano-composite membrane.

2. Description of the Related Art

Direct methanol fuel cells (DMFC) using methanol solution as liquid fuel are a source of future clean energy that can replace fossil energy. Also, a DMFC is workable at room temperature and can be miniaturized and sealed. Thus, the DMFC has a very wide applicability in fields including zero-emission vehicles, home power generating systems, mobile communication equipment, medical appliances, military equipment, and aerospace industrial equipment, as well as in the field of portable electrical devices.

The DMFC is a power generating system that produces direct current by an electrochemical reaction of methanol and oxygen. A basic structure of the DMFC is shown in FIG. 1. Referring to FIG. 1, the DMFC includes a proton conducting membrane 11 interposed between an anode and a cathode.

The proton conducting membrane 11 is mainly made of a solid polymer electrolyte. The anode and the cathode include catalyst layers 12 and 13 formed on a cathode supporting layer 14 and an anode supporting layer 15, respectively. The supporting layers 14 and 15 are made of carbon cloth or carbon paper and their surfaces are treated so that water to be transferred to the proton conducting membrane 11 and water generated by the reaction at the cathode can easily pass therethrough while supplying a reaction gas or liquid. In FIG. 1, a reference numeral 16 represents a bipolar plate having grooves for injecting gas and which acts as a current collector.

When a reaction fuel is supplied to the DMFC having the above-described structure, an oxidation reaction occurs in the anode, wherein methanol and water are converted into carbon dioxide, protons, and electrons. During this process, the protons are transferred to the cathode via the proton conducting membrane 11.

Meanwhile, a reduction reaction occurs in the cathode, wherein oxygen molecules from the air receive the electrons from the anode and are converted into oxygen ions. Then, the oxygen ions react with the protons from the anode to produce water molecules.

In the above DMFC, the proton conducting membrane 11 is a solid polymer membrane and acts as separator of fuels to be supplied to each of the anode and the cathode while transferring the protons produced in the anode to the cathode.

A commercially available perfluorosulfonic acid membrane, sold under the name NAFION (a registered trademark of Dupont, Wilmington, Del.), is commonly used as the solid polymer membrane. It is known that since the solid polymer membrane is formed of a polymer that has a hydrophobic backbone and hydrophilic group-containing side chains, it can contain water. The protons migrate through a cluster formed by water that is contained in the solid polymer membrane. Therefore, it is preferable that in order to effectively transfer the protons, solid polymer membranes having an increased content of water to increase proton conductivity be used.

In a DMFC using an aqueous methanol solution as fuel, swelling of a solid polymer membrane may occur depending on the concentration of methanol in the aqueous methanol solution. Due to the swelling phenomenon, fuel that is not oxidized by an electrochemical reaction migrates from the anode to the cathode through the solid polymer membrane, thereby lowering the performance by creating a mixed potential in the cathode and also by wasting the fuel.

In order to address the above problem, it is desirable to develop an improved solid polymer membrane for DMFCs.

In forming a solid polymer membrane for DMFCs, a method of lowering the permeability of aqueous methanol solution by using rigid and heat-resistant polymers was proposed in U.S. Pat. No. 6,510,047. This method can remarkably lower the permeability of methanol. However, since this method also considerably reduces the ion conductivity of the polymer membrane, the performance, such as power density, of the fuel cell is considerably lowered.

As another method for forming a solid polymer membrane for DMFCs, a method of dispersing an inorganic filler in a polymer membrane was proposed in U.S. Pat. No. 6,059,943. According to this method, the permeability of methanol can be significantly reduced due to mixing of the inorganic filler and polymer. However, the ion conductivity of the polymer membrane is also considerably lowered.

SUMMARY OF THE INVENTION

Aspects of the present invention provide a proton conducting titanate, a method of forming the same, and a polymer nano-composite membrane including the proton conducting titanate, and thus having lower methanol permeability and good ion conductivity.

Aspects of the present invention also provide a fuel cell adopting the polymer nano-composite membrane, and thus having improved fuel efficiency.

According to an aspect of the present invention, there is provided a proton conducting titanate including titanate and a sulfonic acid group-containing moiety having proton conductivity introduced into the surface of the titanate, wherein the sulfonic acid group-containing moiety is directly bound to the titanate via an ether bond (—O—).

The sulfonic acid group-containing moiety may be:

   i)

wherein $R_1$ is a substituted or unsubstituted C1-C12 alkylene group or a substituted or unsubstituted C1-C12 alkenylene group, A is —C(R')(R")— or —C=O—, and R' and R" are each independently hydrogen or C1-C10 alkyl, or R' and R" together form a ring represented by the following formula:

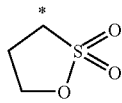

wherein * indicates the position where R' and R" are attached to carbon; or

wherein $R_2$ is —F, —Cl, —$SF_5$, =$SF_4$, —$SF_4Cl$, —$CF_3$, —$CF_2CF_3$, —$H(CF_2)_4$, a C1-C12 alkyl group, a C1-C12 halogenated alkyl group, a C1-C12 alkenyl group, a C1-C12 halogenated alkenyl group, —$CF_2OSO_2F$, —$(CF_2)_4CHFSO_2F$, —$CF_2CF_2CHFSO_2F$, —$CF_2CHFSO_2F$, —$CF_2OCF(CF_3)CF_3$, —$CF_2C(=CF_2)F$, —$CF_2OCF_3$, —$CF_2C(F)(Cl)CF_2CCl_2F$, —$CH_2CH(Cl)CH_2Cl$, or a group represented by the following formula:

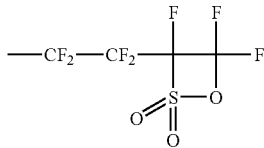

wherein X is —F, —H, —Cl or —$CF_3$, and $Y_1$ and $Y_2$ are each independently F or Cl.

The sulfonic acid group-containing moiety may be —$O(CH_2)nSO_3H$ wherein n is an integer from 1 to 13, or —O—$C(R_2)(X)CF_2SO_3H$ wherein $R_2$ is —F, —$CF_3$, —$SF_5$, =$SF_4$, —$SF_4Cl$, —$CF_2CF_3$ or —$H(CF_2)_4$, and X is —F, —H, —Cl or —$CF_3$.

According to another aspect of the present invention, there is provided a method of preparing a proton conducting titanate, the method including sulfonating titanate by reacting a sultone compound with the titanate in the presence of a solvent.

According to another aspect of the present invention, there is provided a method of preparing a proton conducting titanate, the method including: reacting titanate with an alkoxysilane containing a hydrolysable alkoxy group and a free thiol group in the presence of a solvent to form a reaction product; and conducting an oxidation by adding an oxidizing agent to the reaction product, followed by a protonation.

According to another aspect of the present invention, there is provided a polymer nano-composite membrane including: a proton conducting polymer; and a proton conducting titanate including titanate and a sulfonic acid group-containing moiety having proton conductivity introduced into the surface of the titanate, wherein the sulfonic acid group-containing moiety is directly bound to the titanate via an ether bond (—O—).

According to another aspect of the present invention, there is provided a fuel cell including the polymer nano-composite membrane. The fuel cell may be a direct methanol fuel cell (DMFC).

According to another aspect of the present invention, there is provided a method of preparing titanate, the method including: adding ammonium hydroxide to a mixture of titanium oxysulfate and water; conducting a hydrothermal reaction to obtain a reaction product; filtering the reaction product to obtain precipitates; treating the precipitates with an acid; and drying and heat-treating the resulting product.

Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE EMBODIMENTS

Figure 1:
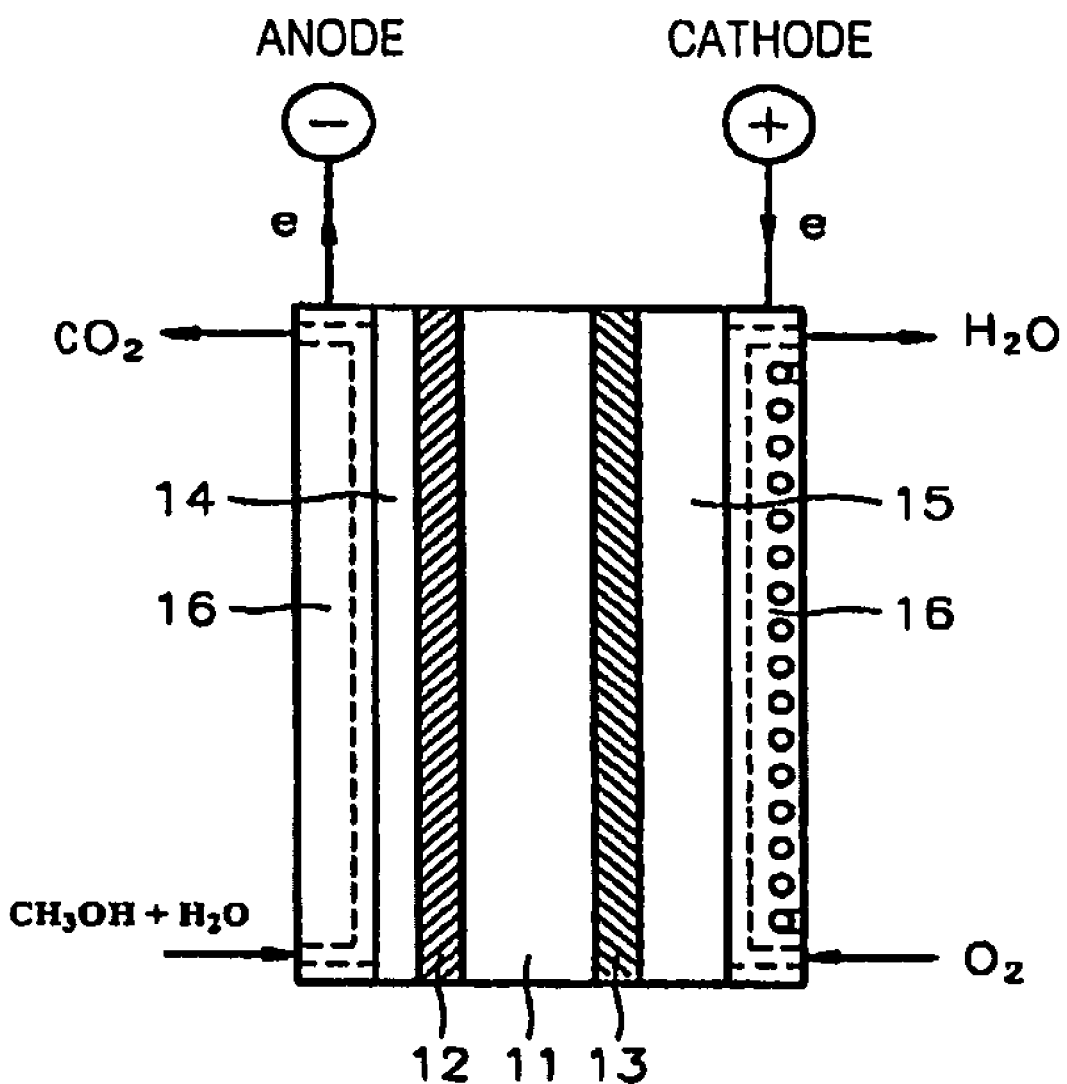
FIG. 1 is a plan view of a structure of a direct methanol fuel cell.

Reference will now be made in detail to the present embodiments of the present invention, examples of which are illustrated in the accompanying drawings, wherein like reference numerals refer to the like elements throughout. The embodiments are described below in order to explain the present invention by referring to the figures.

To minimize a reduction of ion conductivity of an electrolyte membrane due to addition of titanate as an inorganic filler in the preparation of the electrolyte membrane, a functional group having a proton exchange capacity is introduced into the inorganic filler to reduce crossover of methanol and to minimize a reduction of resistance.

Titanate ($H_2Ti_3O_7$) used as an inorganic filler in the present invention may be prepared as follows.

Titanium oxysulfate and water are mixed, and then ammonium hydroxide is slowly added and stirred. The amount of ammonium hydroxide is preferably 2 to 30 mol, more preferably, 3 to 15 mol, based on 1 mol of titanium oxysulfate. When the amount of ammonium hydroxide is less than 2 mol, titanate having a plate-shaped structure is not formed and when the amount of ammonium hydroxide is greater than 30 mol, titanate having a nano-fiber structure is mainly formed.

Aqueous ammonia may be used as a source of the ammonium hydroxide and may have a concentration of 28 to 30 wt %.

Next, a hydrothermal reaction of the mixture is conducted at 100 to 135° C. under a pressure of 1 to 5 atm. When the hydrothermal reaction temperature is lower than 100° C., an amorphous titanate is obtained and a plate-shaped structure is not formed, and when the hydrothermal reaction temperature is higher than 130° C., nano-rods are formed. When the hydrothermal reaction pressure is greater than 5 atm, nano-rods are formed and when the hydrothermal reaction pressure is less than 1 atm, a plate-shaped structure is not formed.

After the hydrothermal reaction is completed, precipitates formed in the reaction mixture are filtered and washed with a solvent such as water or ethanol. The obtained precipitates are treated with an acid. The acid used in the present invention may be hydrochloric acid or sulphuric acid. In an embodiment of the present invention, a 0.5 N aqueous HCl solution is used.

Subsequently, the acid-treated product is dried and heat-treated to obtain the desired titanate.

The drying is carried out at 25 to 85° C. and the heat-treating is carried out at 350 to 500° C.

As described above, titanate having an anatase-type crystal structure can be synthesized without using a surfactant. The morphology of the titanate may be nanosheet, nanofiber or a mixture thereof and is varied according to factors such as the hydrothermal reaction temperature, the mol ratio of reactants, and the like. As non-limiting examples, the nanosheet may have a surface area of about 374 m$^2$/g and a pore volume of about 0.56 cm$^3$/g and has a plate-shaped structure. The nanofiber may have a surface area of about 512 m$^2$/g and a pore volume of about 0.72 cm$^3$/g and has a fiber structure. The titanate having the above-described morphology may have a length of about 200 nm, a diameter of 8 to 10 nm and an aspect ratio of 10 to 25. Due to such a morphology, a degree of swelling can be reduced in a polymer composite membrane using the titanate.

The titanate useful in the preparation of the proton conducting titanate according to an embodiment of the present invention is subjected to a hydrothermal reaction at about 120° C., and thus has morphology of a mixture of nanosheets and nanofibers, which is preferable in that a reduction of methanol crossover in a polymer composite membrane may be optimized. The mixing ratio of the nanosheets and nanofibers may be 10:90 to 90:10. Here, the mixing ratio may be based on weight, mol or volume, but is preferably based on volume.

A sulfonic acid group-containing moiety having proton conductivity is introduced into the surface of the titanate obtained as described above. The sulfonic acid group-containing moiety is directly bound to the titanate via an ether bond (—O—) to form a proton conducting titanate. A method of preparing the proton conducting titanate will be described in more detail below.

A compound useful for introduction of the sulfonic acid group-containing moiety may be a sultone compound or an alkoxysilane containing a hydrolysable alkoxy group and a free thiol group. A method of preparing a proton conducting titanate using a sultone compound will now be described.

First, titanate, a solvent, and a sultone compound are mixed and refluxed.

The sultone compound may be a sultone compound represented by Formula 1 or a fluorinated sultone compound represented by Formula 2:

Formula 1

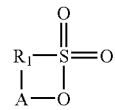

wherein $R_1$ is a substituted or unsubstituted C1-C12 alkylene group or a substituted or unsubstituted C1-C12 alkenylene group, A is —C(R')(R")— or —C=O—, and R' and R" are each independently hydrogen or a C1-C10 alkyl group, or R' and R" together form a ring represented by the following formula:

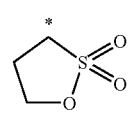

wherein * indicates the position where R' and R" are attached to carbon; and

Formula 2

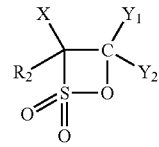

wherein $R_2$ is —F, —Cl, —SF$_5$, =SF$_4$, —SF$_4$Cl, —CF$_3$, —CF$_2$CF$_3$, —H(CF$_2$)$_4$, a C1-C12 alkyl group, a C1-C12 halogenated alkyl group, a C1-C12 alkenyl group, a C1-C12 halogenated alkenyl group, —CF$_2$OSO$_2$F, —(CF$_2$)$_4$CHFSO$_2$F, —CF$_2$CF$_2$CHFSO$_2$F, —CF$_2$CHFSO$_2$F, —CF$_2$OCF(CF$_3$)CF$_3$, —CF$_2$C(=CF$_2$)F, —CF$_2$OCF$_3$, —CF$_2$C(F)(Cl)CF$_2$CCl$_2$F, —CH$_2$CH(Cl)CH$_2$Cl, or a group represented by the following formula:

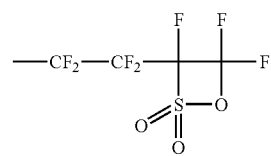

wherein X is —F, —H, —Cl or —CF$_3$, and Y$_1$ and Y$_2$ are each independently F or Cl.

Examples of the sultone compound such as the sultone compound represented by Formula 1 include 1,3-propanesultone (A), 1,4-butanesultone (B), and compound (C) through compound (S) represented by the following formulae:

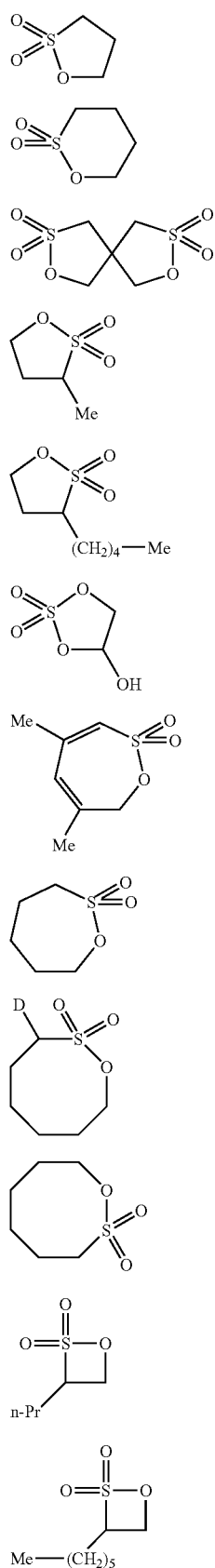
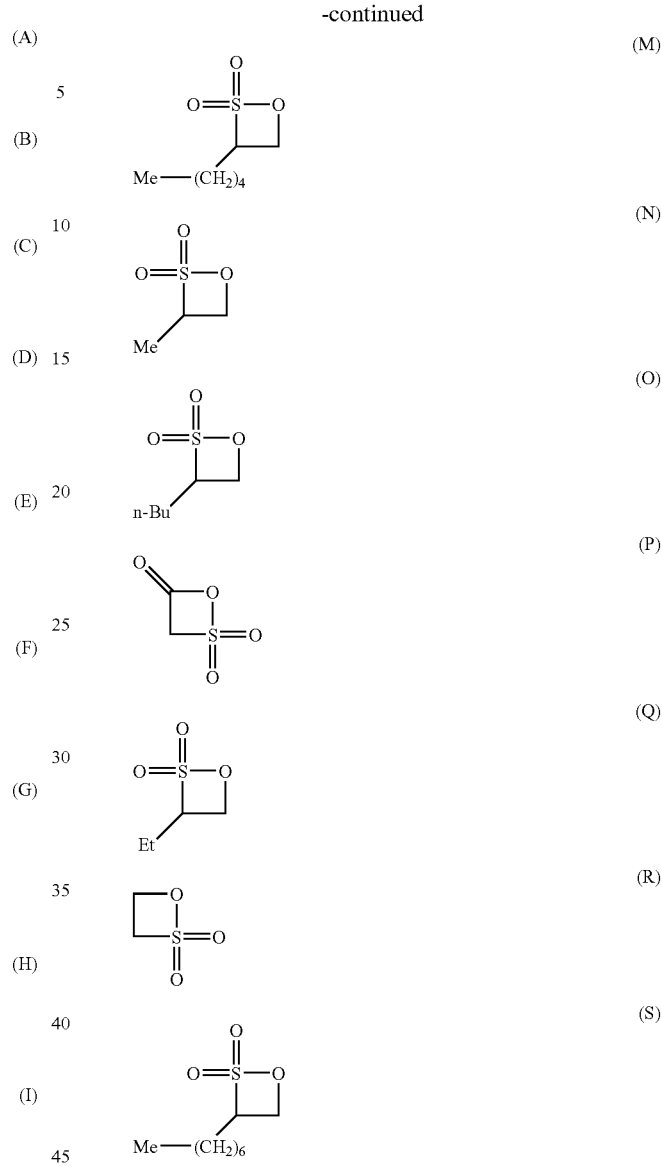

Examples of the fluorinated sultone compound represented by Formula 2 include 1-trifluoromethyl-1,2,2-trifluoroethanesulfonic acid sultone (A'), 1-trifluoromethyl-2,2-bifluoroethanesulfonic acid sultone (B'), 4H-perfluorobutyl-1,2,2-trifluoroethanesulfonic acid sultone (C'), compound (D') through compound (Z'), and compound (a') through compound (b') represented by the following formulae:

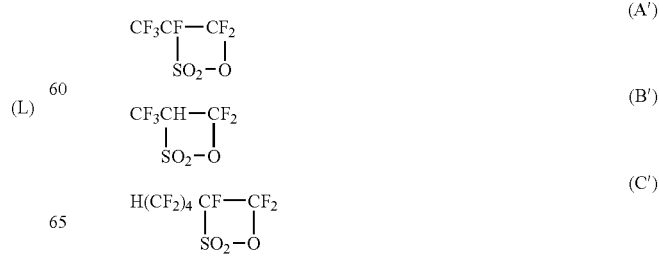

-continued
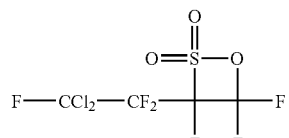
(D')
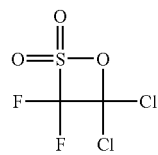
(E')
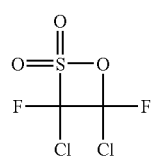
(F')
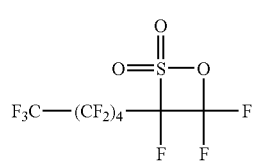
(G')
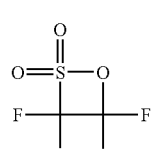
(H')
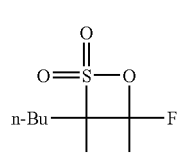
(I')
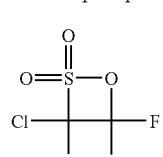
(J')
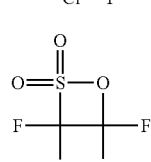
(K')
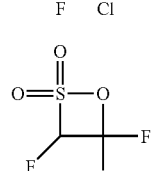
(L')
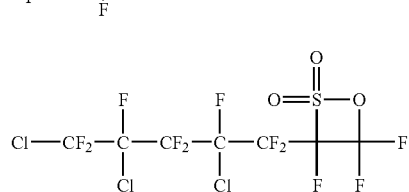
(M')
-continued
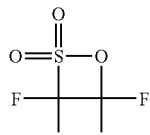
(N')
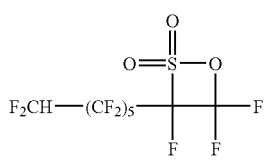
(O')
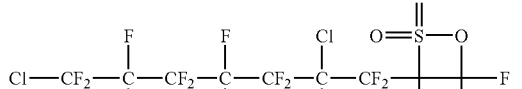
(P')
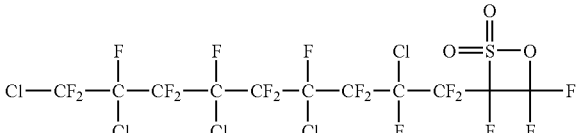
(Q')
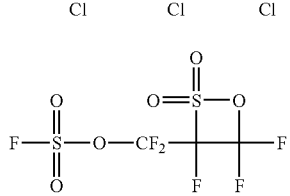
(R')
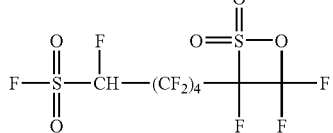
(S')
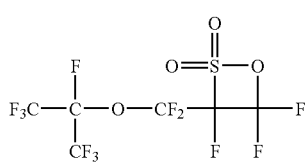
(T')
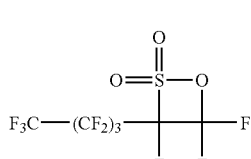
(U')
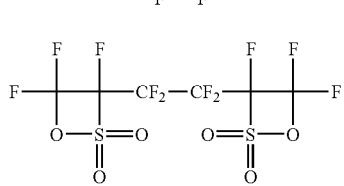
(V')

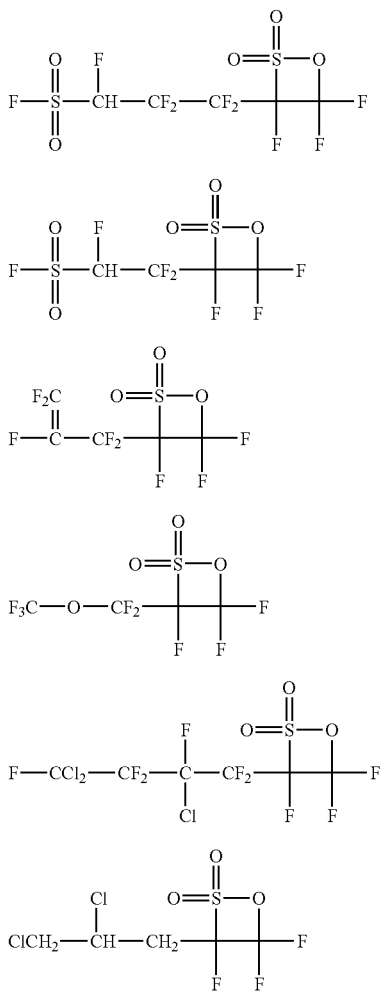

The ion exchange capacity (IEC) of the sultone compound may range from 0.01 to 5 mmol/g.

The amount of the sultone compound may be 5 to 40 parts by weight, preferably 10 to 30 parts by weight, based on total 100 parts by weight of the titanate and the sultone compound. When the amount of the sultone compound is less than 10 parts by weight, the ion conductivity of the proton conducting titanate is poor. When the amount of the sultone compound exceeds 30 parts by weight, it is not cost-effective.

A solvent capable of dissolving or dispersing the titanate may be used. Examples of such a solvent include toluene, hexane and dimethylformamide (DMF). The content of the solvent may be in the range of 50 to 150 parts by weight based on 100 parts by weight of the titanate. The reflux temperature may vary according to the type of solvent, but may be in the range of 100 to 130° C.

After the reaction is completed, the product is filtered and washed with at least one of water and ethanol.

Then, the washed product is dried to obtain the desired proton conducting titanate. The drying is carried out at 25 to 85° C.

When the sultone compound of Formula 1 is used as the reactant sultone compound in the preparation of the proton conducting titanate, an —O—AR$_1$SO$_3$H group is introduced to the surface of the titanate as the sulfonic acid group-containing moiety that is directly bound to the titanate via an ether bond. In the above formula, R$_1$ is a substituted or unsubstituted C1-C12 alkylene group, or a substituted or unsubstituted C1-C12 alkenylene group, and A is —C(R')(R")— or —C=O— [wherein R' and R" are each independently hydrogen or a C1-C10 alkyl group, or R' and R" together may form a ring represented by the following formula:

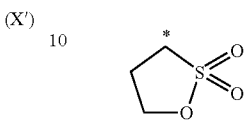

(wherein * indicates the position where R' and R" are attached to carbon)].

When the sultone compound of Formula 2 is used as the reactant sultone compound, an —O—C(R$_2$)(X)C(Y$_1$)(Y$_2$)SO$_3$H group is introduced to the surface of the titanate as the sulfonic acid group-containing moiety that is directly bound to the titanate via an ether bond.

In the above formula, R$_2$ is —F, —Cl, —SF$_5$, =SF$_4$, —SF$_4$Cl, —CF$_3$, —CF$_2$CF$_3$, —H(CF$_2$)$_4$, C1-C12 alkyl, C1-C12 halogenated alkyl, C1-C12 alkenyl, C1-C12 halogenated alkenyl, —CF$_2$OSO$_2$F, —(CF$_2$)$_4$CHFSO$_2$F, —CF$_2$CF$_2$CHFSO$_2$F, —CF$_2$CHFSO$_2$F, —CF$_2$OCF(CF$_3$)CF$_3$, —CF$_2$C(=CF$_2$) F, —CF$_2$OCF$_3$, —CF$_2$C(F)(Cl) CF$_2$CCl$_2$F, —CH$_2$CH(Cl)CH$_2$Cl, or a group represented by the following formula:

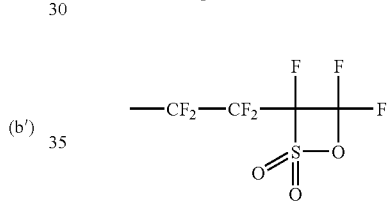

wherein X is —F, —H, —Cl or —CF$_3$; and Y$_1$ and Y$_2$ are each independently F or Cl.

The sulfonic acid group-containing moiety that is directly bound to the titanate via an ether bond may be —O—(CH$_2$)$_n$SO$_3$H, wherein n is an integer from 1 to 13, or —O—C(R$_2$)(X)CF$_2$SO$_3$H, wherein R$_2$ is —F, —CF$_3$, —SF$_5$, =SF$_4$, —SF$_4$Cl, —CF$_2$CF$_3$ or —H(CF$_2$)$_4$, and X is —F, —H, —Cl or —CF$_3$.

Figure 2:
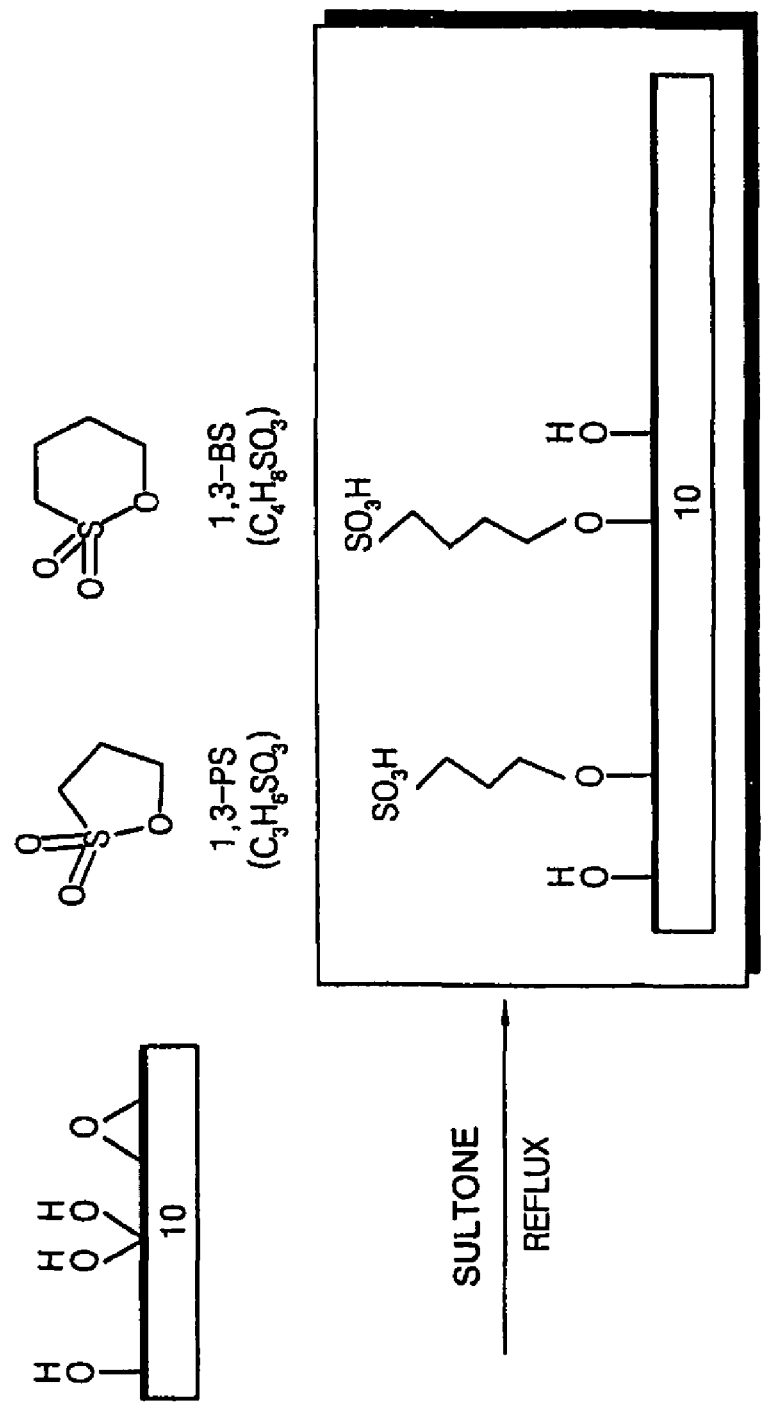
FIG. 2 is a schematic diagram illustrating a process of preparing a proton conducting titanate having a layered structure according to an embodiment of the present invention.

FIG. 2 is a diagram of a process of preparing the proton conducting titanate described above.

Referring to FIG. 2, —OH groups positioned at the surface of titanate 10 react with a sultone compound, which allows a sulfonic acid group-containing moiety to be introduced into the surface of the titanate 10. The sulfonic acid group-containing moiety is directly bound to the titanate via an ether bond (—O—) to provide a proton conducting titanate.

A method of preparing a proton conducting titanate using an alkoxysilane containing a hydrolysable alkoxy group and a free thiol group will now be described.

Titanate, an alkoxysilane containing a hydrolysable alkoxy group and a free thiol group, and a solvent are mixed and refluxed. Through the hydrolysis of the alkoxysilane and dehydration and condensation of the hydrolysed product, silicate, which is connected to one layer of the titanate via ether bond and has a free thiol group at the terminal, is introduced onto the surface or between layers of the titanate.

Non-limiting examples of the alkoxysilane containing a hydrolysable alkoxy group and a thiol group include 3-mercaptopropyl trimethoxysilane (3-MPTMS) represented by Formula 8, 3-mercaptopropyl methyl dimethoxysilane (3-MPDMS) represented by Formula 9, and a mixture thereof.

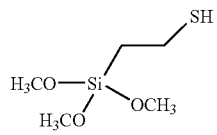

Formula 8

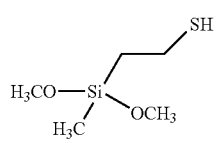

Formula 9

The content of the alkoxysilane is in the range of 0.1 to 2 mol based on 1 mol of the titanate. Or the content of the alkoxysilane is in the range of 5 to 40 parts by weight based on total 100 parts by weight of the alkoxysilane and the titanate. When the content of the alkoxysilane is less than 0.1 mol, the inorganic material has too low of an ion exchange capacity (IEC). On the other hand, when the content of the alkoxysilane is greater than 2 mol, the saturation thereof is excessive, thereby increasing the processing cost.

The reaction of the titanate and the alkoxysilane may be carried out at 100 to 180° C. When the reaction temperature does not lie within the above range, the reactants may be decomposed or no reaction may occur.

Toluene, hexane or DMF is used as a solvent similar to the reaction using the sultone compound. The content of the solvent may be in the range of 50 to 150 parts by weight based on 100 parts by weight of the titanate.

Then, the reaction product of the titanate and the alkoxysilane is reacted with an oxidizing agent and protonated to convert the free thiol group at the terminal into a sulfonic acid group. As a result, a proton conducting titanate having a layered structure is completed.

$H_2O_2$, $K_2O_2$, or $BaO_2$ may be used as the oxidizing agent and the amount of the oxidizing agent may be in the range of from 0.5 to 5 mol based on 1 mol of the titanate.

The oxidation is preferably carried out at a temperature of 25 to 60° C. When the temperature does not lie within the above range, oxidation does not occur or decomposition occurs.

The proton conducting titanate obtained through the process described above is subjected to purification and drying before being used in the production of a polymer nano-composite membrane.

The polymer nano-composite membrane according to an embodiment of the present invention is prepared through a reaction between the proton conducting titanate and a proton conducting polymer. To be more specific, the proton conducting titanate and the proton conducting polymer are mixed through vigorous stirring at a temperature of 60 to 150° C. for 12 hours or more, and then are allowed to react.

The reaction time may vary depending on the reaction temperature, but the reaction time may be, for example, 1 to 2 days. When the reaction temperature is lower than 60° C., the mixing state of the proton conducting titanate and the proton conducting polymer is poor, and when the reaction temperature is higher than 150° C., the proton conducting titanate tends to decompose, which is undesirable.

In the reaction described above, for example, the polymer nano-composite membrane according to an embodiment of the present invention can be prepared by mixing the proton conducting titanate and the proton conducting polymer at a particular predetermined mixing ratio, and then allowing the titanate and the polymer to react in an autoclave at 80° C. and 1 to 5 atm for 12 hours or more. Alternatively, the polymer nano-composite membrane can be prepared by mixing the proton conducting titanate and a solution containing the proton conducting polymer, subsequently mixing the resulting mixture more thoroughly in a homogenizer for 30 minutes or more, and then allowing the proton conducting titanate and the proton conducting polymer to react at 60 to 150° C.

After completion of the reaction between the proton conducting titanate and the proton conducting polymer, the reaction mixture is placed in a mold for a polymer membrane and kept in an oven that is maintained at a temperature ranging from 80 to 150° C. to obtain the polymer nano-composite membrane.

Non-limiting examples of the proton conducting polymer include perfluorinated sulfonic acid polymers, sulfonated polyimides, sulfonated polyether ketones, sulfonated polystyrenes, sulfonated polysulfones, and combinations thereof. The ion exchange capacity of the proton conducting polymer is in the range of 0.01 mmol/g to 5 mmol/g.

The amount of the proton conducting polymer may be 400 to 3500 parts by weight based on 100 parts by weight of the proton conducting titanate having a layered structure. When the amount of the proton conducting polymer does not lie within the above-described range, film formation may not be achieved satisfactorily.

The polymer nano-composite membrane prepared as described above has a thickness of 20 to 200 μm, which is suitable for its adoption in fuel cells.

The polymer nano-composite membrane can be used as a proton conducting membrane in a fuel cell such as the fuel cell illustrated in FIG. 1.

In order to obtain the most efficient performance by applying the polymer nano-composite membrane to the fuel cells, the polymer nano-composite membrane can be subjected to a pretreatment. This pretreatment process helps the polymer nano-composite membrane sufficiently absorb moisture and smoothly undergo activation, and includes boiling the polymer nano-composite membrane in deionized water for about 2 hours, or boiling the polymer nano-composite membrane in a dilute sulfuric acid solution for about 2 hours and then boiling the polymer nano-composite membrane again in deionized water.

The process of preparing a membrane and electrode assembly for a fuel cell using the polymer nano-composite membrane thus pretreated is as follows. The term "membrane and electrode assembly (MEA)" as used herein refers to a structure in which a proton conducting polymer membrane is located in the center, and a catalyst layer and an electrode are sequentially laminated on both sides thereof.

The MEA of the present invention is formed by locating an electrode, which has a catalyst layer, on both sides of the polymer membrane, and then joining the electrode and the polymer membrane at high temperature and high pressure, or by coating the polymer membrane with a catalyst metal that catalyzes an electrochemical catalytic reaction, and then joining a fuel diffusing layer thereto.

The joining temperature and pressure are a temperature at which the proton conducting membrane is softened (about 125° C. for NAFION) and a pressure of 0.1 to 1 ton/cm$^2$, in particular, about 1 ton/cm$^2$. The electrode may be a conducting carbon cloth or a carbon paper layer. Then, the MEA is provided with bipolar plates, respectively, on both sides thereof to complete a fuel cell. The bipolar plates have grooves for supplying fuel and act as current collectors.

In the preparation of the MEA, Pt alone, or an alloy or a mixture of Pt and at least one of metal among Au, Pd, Rh, Ir, Ru, Sn and Mo may be used as the catalyst.

The present invention will be described in greater detail with reference to the following examples. The following examples are for illustrative purposes and are not intended to limit the scope of the invention.

PREPARATION EXAMPLE 1

Synthesis of Titanate 16 g of titanium oxysulfate and 20 ml of water were mixed for 1 hour, and then 28-30 wt % ammonia water was slowly added thereto. The content of ammonium hydroxide in the aqueous ammonia was about 5 mol based on 1 mol of titanium oxysulfate.

The mixture was stirred at room temperature (25° C.) for 1 hour, and then a hydrothermal reaction was conducted at 3.5 atm and 140° C. for about 3 days.

After the reaction was completed, the reaction mixture was filtered and washed with water and ethanol. Next, 0.5 N HCl was added to the resulting product to form precipitates. The precipitates were filtered and dried at room temperature, and then dried at 80° C. for 24 hours.

Subsequently, the dried solid was calcined in the air at 400° C. for 4 hours to obtain titanate. The calcining heating rate was about 2° C./min.

PREPARATION EXAMPLE 2

Synthesis of Titanate

Titanate was prepared in the same manner as in Preparation Example 1 except that the mol ratio of ammonium hydroxide to titanium oxysulfate was 15.

The titanate prepared in Preparation Example 1 had a morphology of a complex of a nanosheet and a nanofiber, a length of about 200 nm, a diameter of 8 to 10 nm, and an aspect ratio of 10 to 25.

Figure 3:
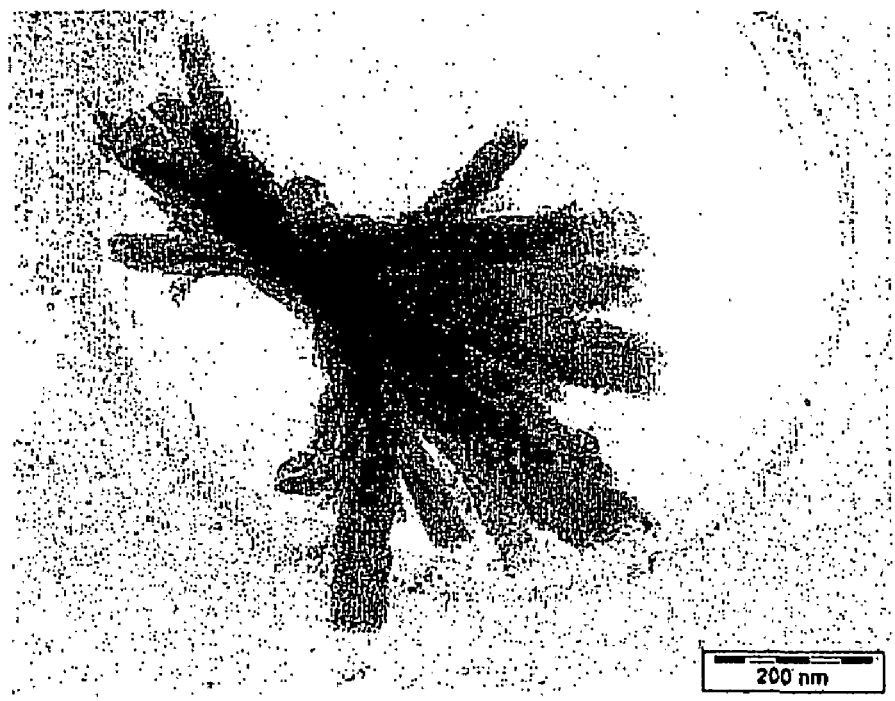
FIGS. 3 and 4 are transmission electron microscopic (TEM) images of titanates prepared in Preparation Examples 1 and 2.
Figure 4:
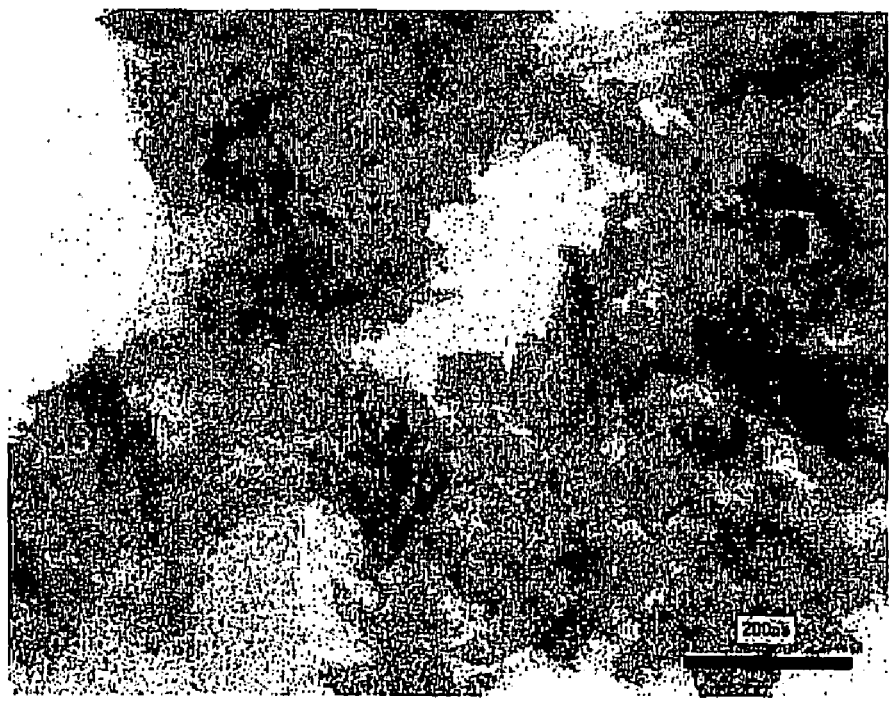

FIGS. 3 and 4 are transmittance electron microscopic (TEM) images of titanates prepared in Preparation Examples 1 and 2. FIG. 3 is an image of the titanate in which the mol ratio of ammonium hydroxide to titanium oxysulfate is 5 and FIG. 4 is an image of the titanate in which the mol ratio of ammonium hydroxide to titanium oxysulfate is 15.

Titanates shown in FIGS. 3 and 4 are $(NH_4)_2Ti_3O_7$, which is protonated into $H_2Ti_3O_7$.

EXAMPLE 1

Preparation of Proton Conducting Titanate Using 1,3-propane sultone (1,3-PS)

An amount of 150 ml of toluene was added to 500 ml round-bottom flask and purged with $N_2$, followed by adding 7.73 g of the titanate prepared in Preparation Example 1 and stirring.

Then, 1.839 of 1,3-propanesultone was added to the mixture. The reaction mixture was stirred at 110° C. for 24 hours.

The reaction mixture was cooled, filtered, washed with ethanol, and dried at room temperature to prepare a proton conducting titanate.

EXAMPLE 2

Preparation of Proton Conducting Titanate Using 1,4-butane sultone (1,4-BS)

A proton conducting titanate was prepared in the same manner as in Example 1 except that 2.04 g of 1,4-butane sultone was used instead of 1.83 g of 1,3-propane sultone.

EXAMPLE 3

Preparation of Proton Conducting Titanate Using 3-mercapto propyl dimethoxymethylsilane (3-MPDMS)

An amount of 150 ml of toluene was added to a 500 ml round-bottom flask and purged with $N_2$, followed by adding 7.73 g of the titanate prepared in Preparation Example 1 and stirring. Then, 2.70 g of 3-MPDMS was added to the mixture. The reaction mixture was mixed at room temperature for 1 hour, followed by raising the temperature thereof to 100° C. and mixing for 24 hours. The reaction mixture was cooled, filtrated, and washed with ethanol, followed by drying in an oven controlled at 60° C.

The dried product was added to a 100 ml flask containing 8.33 g of hydrogen peroxide, and then mixed at room temperature for 6 hours. After raising the temperature of the reaction mixture to 70° C., the reaction was carried out for 1 hour.

After completing the above reaction, the resulting product was filtered, washed with water, and then dried at room temperature. Then, the dried product was poured into a 10 wt % aqueous solution of sulfuric acid and stirred at room temperature for 30 minutes, followed by filtering, washing and drying to prepare a proton conducting inorganic material.

EXAMPLE 4

Preparation of Proton Conducting Titanate Using 3-mercapto propyl trimethoxymethylsilane (3-MPTMS)

A proton conducting titanate was prepared in the same manner as in Example 3 except that 2.94 g of 3-MPTMS was used instead of 1.83 g of 1,3-propane sultone.

Figure 5:
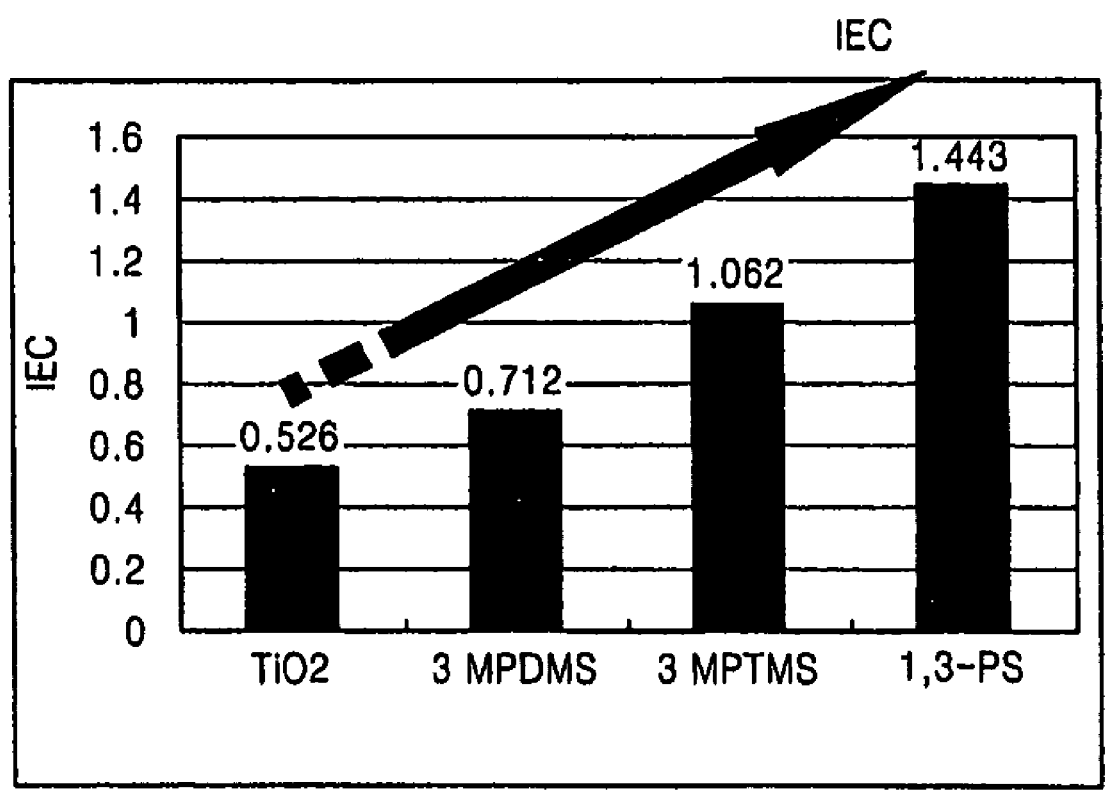
FIG. 5 is a graph illustrating analysis results for ion exchange capacity (IEC) of proton conducting titanates prepared in Examples 1, 3, and 4.

The ion exchange capacity (IEC) of the proton conducting titanates prepared in Examples 1, 3, and 4 was investigated and the results are illustrated in FIG. 5. The IEC was determined by calculating the mol of sulfonic acid through back titration using an aqueous HCl solution and calculating the mmol of sulfonic acid with respect to the weight (g) of the proton conducting titanate.

The proton conducting titanates prepared in Examples 1 through 4 were analyzed through X-ray photoelectron spectroscopy (XPS).

Figure 6:
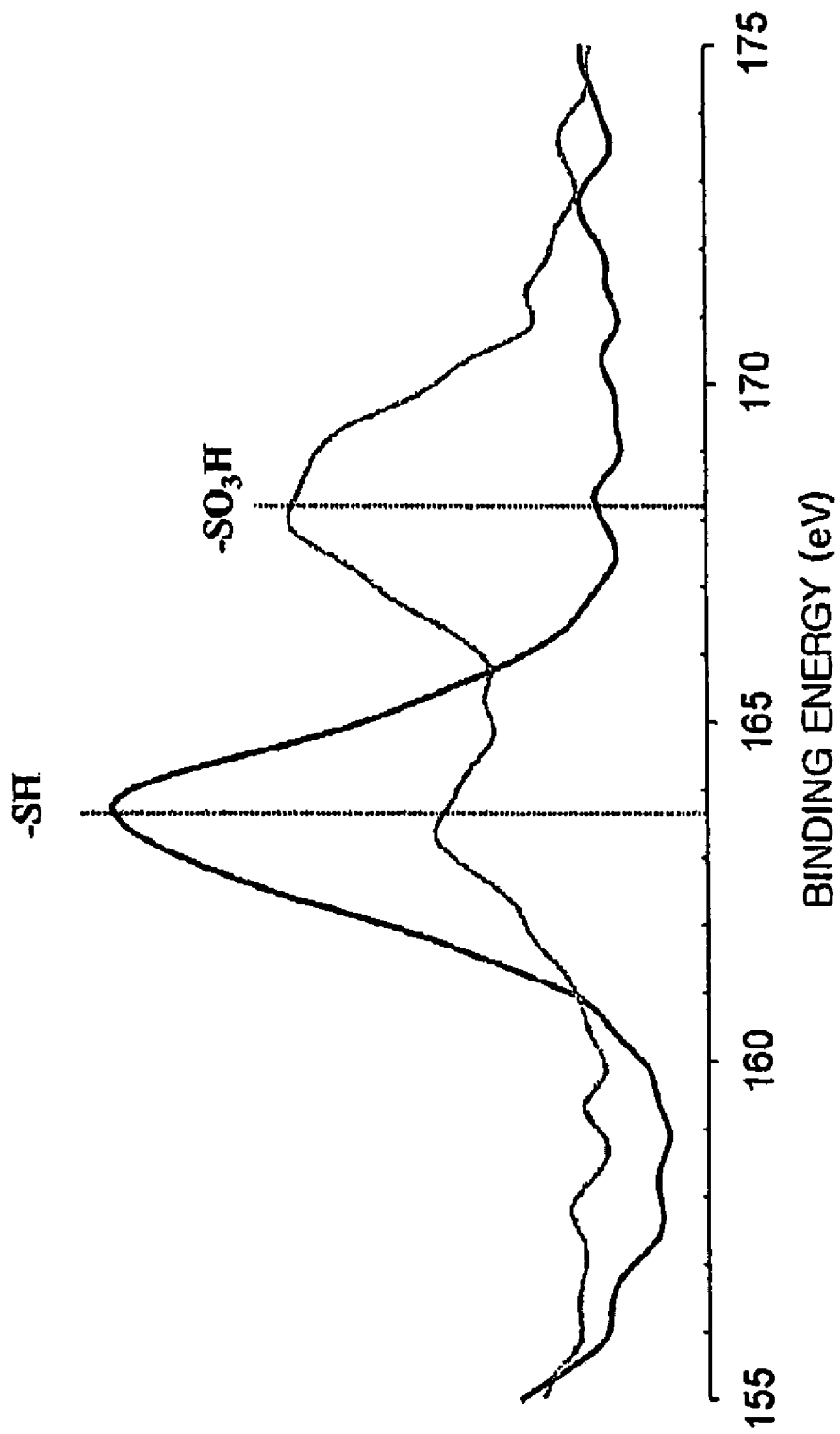
FIG. 6 is an X-ray photoelectron spectroscopy (XPS) diagram of a thiol group and a sulfonic acid group.

FIG. 6 illustrates the XPS analysis results for a thiol group and a sulfonic acid group. Referring to FIG. 6, the thiol group exhibits a maximum absorption peak at a bonding energy of 162.7 eV and the sulfonic acid group exhibits a maximum absorption peak at a bonding energy of 168.6 eV.

Figure 7:
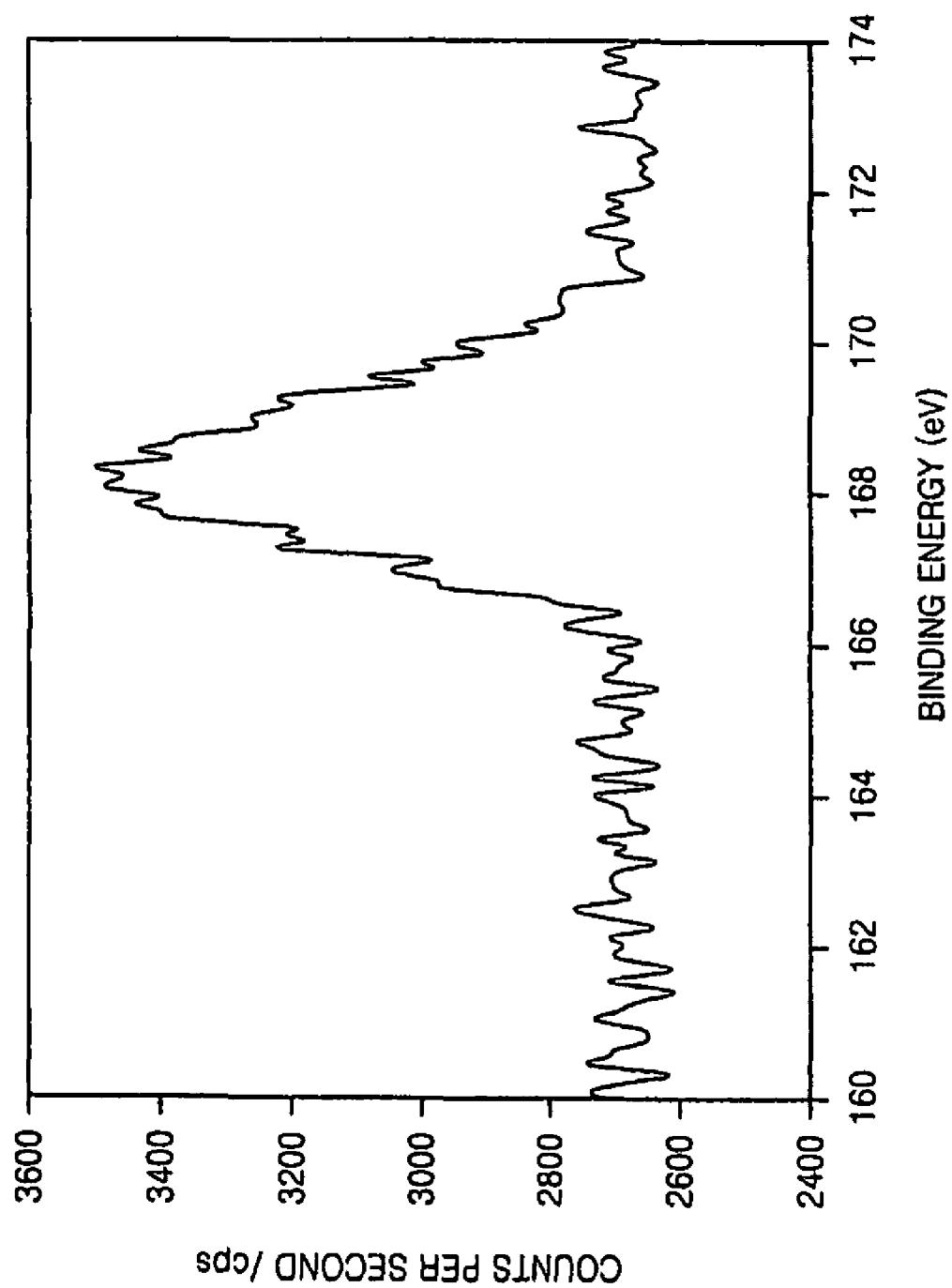
FIG. 7 is an XPS diagram of the proton conducting titanate prepared in Example 1.

FIG. 7 shows the XPS analysis results for the proton conducting titanate prepared in Example 1. It can be seen from the results that the content of sulfur (S) in the proton conducting titanate was about 1.443% by atom.

Furthermore, as a result of XPS analysis of the proton conducting titanates prepared in Examples 2 through 4, it can be seen that the sulfonic acid group content is similar to that of Example 1.

Thermal gravimetric analysis (TGA) was carried out to confirm the thermal stability of the proton conducting titanates prepared in Examples 1 and 4. The TGA results are illustrated in FIGS. 8 and 9.

Figure 8:
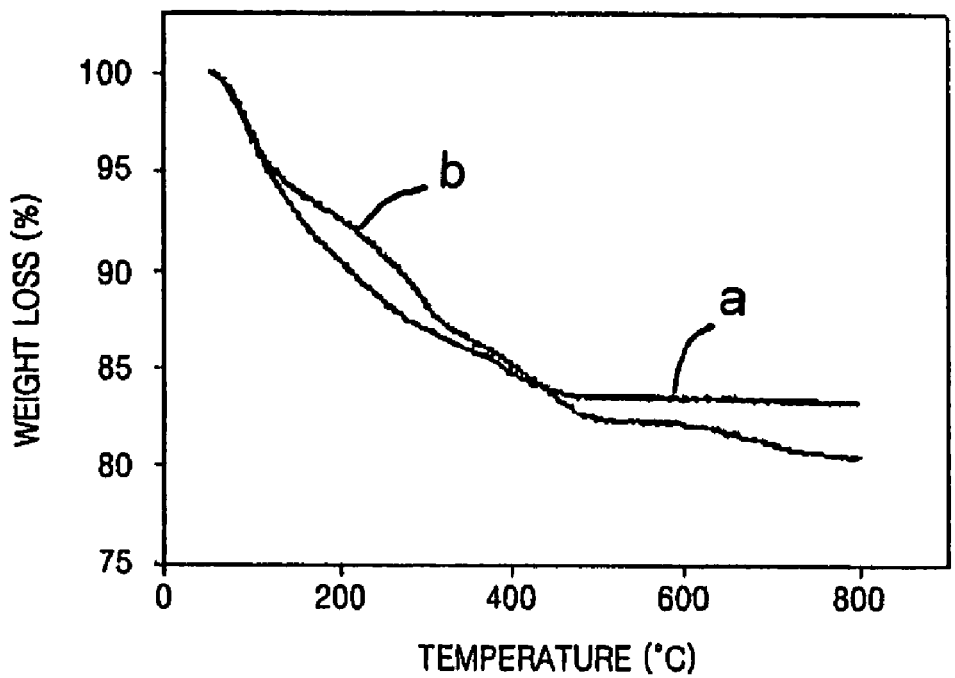
FIGS. 8 and 9 are thermal gravimetric analysis graphs verifying the thermal stability of proton conducting titanates prepared in Examples 1 and 4.
Figure 9:
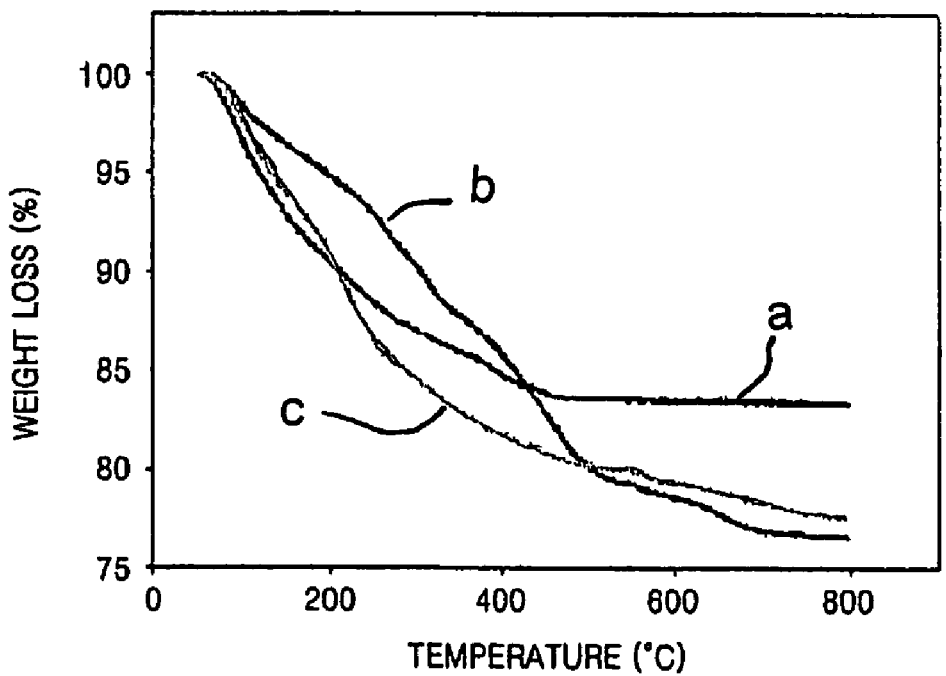

Referring to FIGS. 8 and 9, a weight loss of about 6 wt % at 50 to 100° C. is due to moisture between layers of the inorganic material. The proton conducting titanate prepared in Example 4 has a weight loss of 13 wt % at 250 to 500° C. since 7.97% of the weight loss to due to separation of the thiol group due to thermal decomposition.

FIG. 8 is a graph illustrating the thermal analysis results of the inorganic material prepared in Example 1 and FIG. 9 is a graph illustrating the thermal properties of the proton conducting titanate prepared in Example 1. In FIGS. 8 and 9, "a" represents the thermal gravimetric analysis (TGA) result of the starting material for forming the proton conducting titanate, "b" represents the TGA result of the proton conducting titanate prepared in Example 1, and "c" (FIG. 9 only) represents the TGA result of the proton conducting titanate prepared in Example 4. In the preparation process of the proton conducting titanate of Example 4, an $SO_3H$ percentage is 7.93% after sulfonation and 1.062% after an oxidation by $H_2O_2$, indicating that an S percentage is reduced due to the oxidation. In the case of Example 1, since the $SO_3H$ group can be obtained without the oxidation by $H_2O_2$, a relatively high $SO_3H$ percentage can be obtained compared to Example 4. That is, introduction of a functional group by use of a sultone is advantageous.

EXAMPLE 5

Preparation of Polymer Nano-Composite Membrane 3 parts by weight of the proton conducting titanate prepared in Example 1 was thoroughly mixed with 18.50 g of a 5 wt % NAFION solution, i.e., 97 parts by weight of polymer and heated to 90° C., followed by vigorous stirring at a rate of 900 rpm.

Then, the reaction mixture was stirred for 3 days and transferred to a frame for a polymer membrane, followed by heating in an oven controlled at 120° C. for 4 hours to prepare a polymer nanocomposite membrane.

EXAMPLE 6

Preparation of Polymer Nano-Composite Membrane

A polymer nano-composite membrane was prepared in the same manner as in Example 5 except that 5 parts by weight of the proton conducting titanate and 95 parts by weight of polymer were used instead of 3 parts by weight of the proton conducting titanate and 97 parts by weight of polymer.

EXAMPLE 7

Preparation of Polymer Nano-Composite Membrane

A polymer nano-composite membrane was prepared in the same manner as in Example 5 except that 7 parts by weight of the proton conducting titanate and 93 parts by weight of polymer were used instead of 3 parts by weight of the proton conducting titanate and 97 parts by weight of polymer.

EXAMPLE 8

Preparation of Polymer Nano-Composite Membrane

A polymer nano-composite membrane was prepared in the same manner as in Example 5 except that 10 parts by weight of the proton conducting titanate and 90 parts by weight of polymer were used instead of 3 parts by weight of the proton conducting titanate and 97 parts by weight of polymer.

EXAMPLE 9

Preparation of Polymer Nano-Composite Membrane

A polymer nano-composite membrane was prepared in the same manner as in Example 5 except that the proton conducting titanate prepared in Example 4 was used instead of the proton conducting titanate prepared in Example 1.

EXAMPLE 10

Manufacture of Fuel Cell

The polymer nano-composite membranes prepared in Examples 5-8 were used to prepare a MEA. Then, the resulting MEA was used to prepare a direct methanol fuel cell, in which 2M methanol solution and air were used as fuel.

EXAMPLES 11-14

Manufacture of Fuel Cell

Fuel cells were manufactured in the same manner as in Example 10 except that the polymer nano-composite membranes prepared in Examples 6-9 were used instead of the polymer nano-composite membrane prepared in Example 5.

COMPARATIVE EXAMPLE 1

A polymer membrane and a MEA using the polymer membrane were prepared in the same manner as in Example 10 except that 97 parts by weight of a NAFION 115 membrane (available from Dupont), 18.50 g of a 5 wt % NAFION solution and 3 parts by weight (0.3 g) of montmorillonite were mixed.

Then, the resulting MEA was used to manufacture a direct methanol fuel cell, in which a 2M methanol solution and air were used as fuel.

The MEAs prepared in Examples 10-14 were used in fuel cells to evaluate properties thereof as follows.

Figure 10:
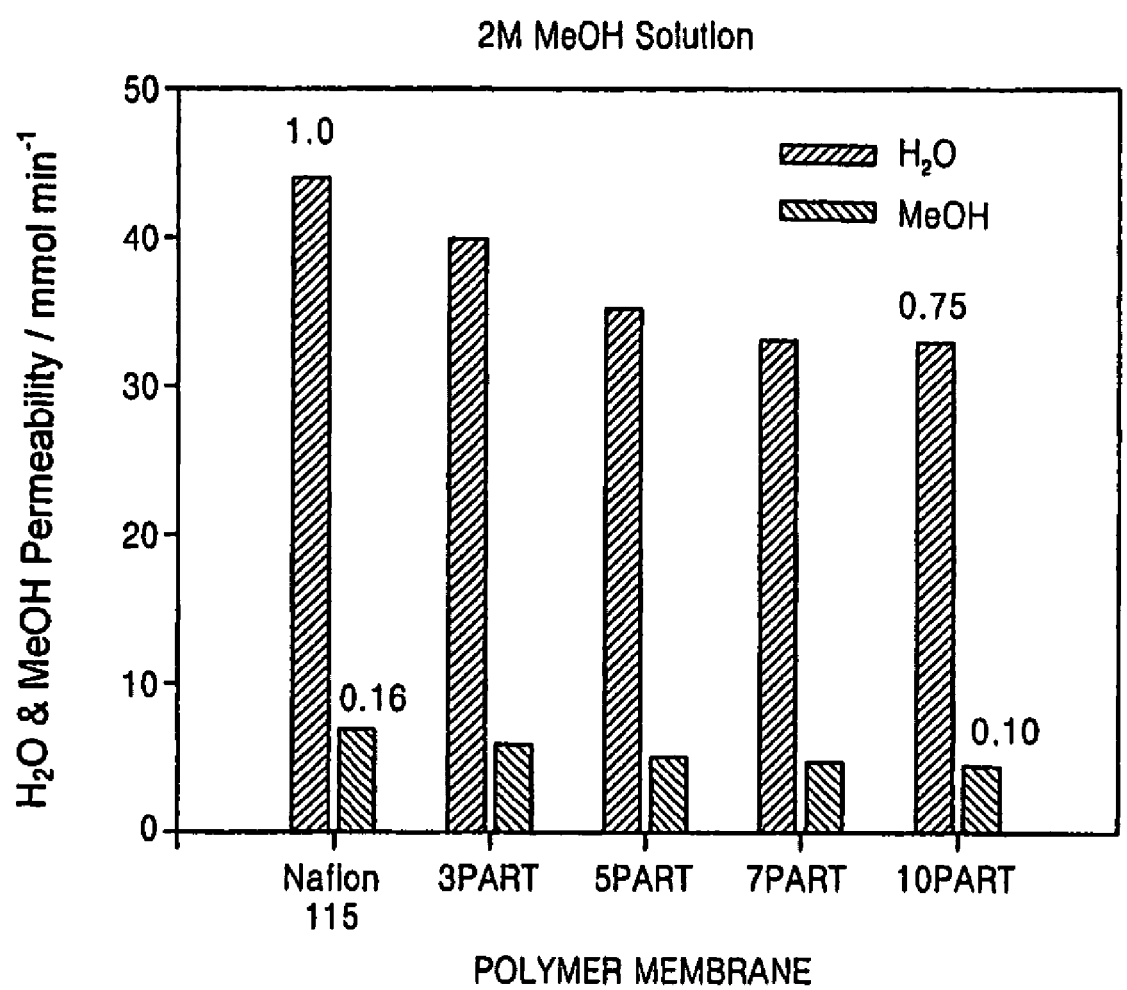
FIGS. 10 and 11 are graphs illustrating permeability to water and methanol of polymer nano-composite membranes prepared in Examples 5-8 and of a polymer membrane of Comparative Example 1.
Figure 11:
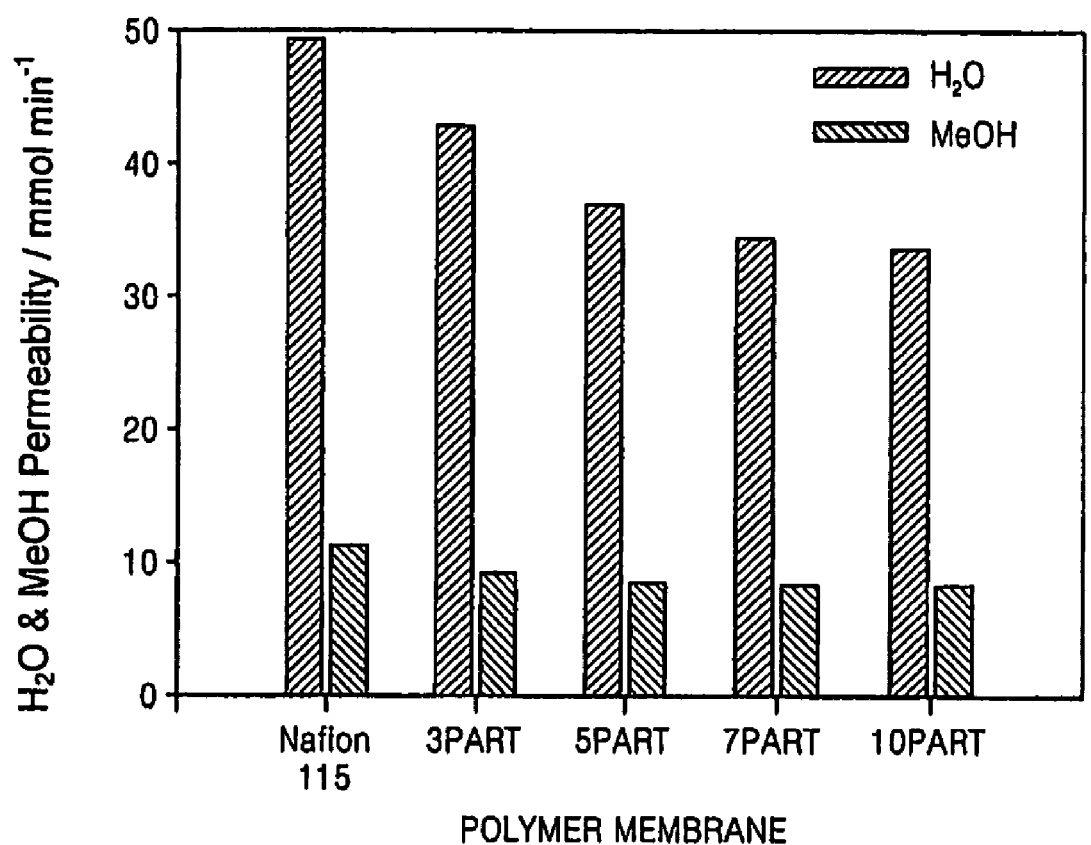

In the polymer nano-composite membranes of Examples 5-8 and the polymer membrane of Comparative Example 1, the permeability of water and methanol was measured. The permeability of water and methanol is shown in FIGS. 10 and 11. FIG. 10 is the permeability for a 2M methanol solution and FIG. 11 is the permeability for a 5M methanol solution. In FIGS. 10 and 11, the results for NAFION 115 is also shown to compare with the results of the polymer nano-composite membranes of Example 5-8.

Referring to FIGS. 10 and 11, it is apparent that the polymer nanocomposite membranes of Examples 5-8 have a lowered permeability compared to the NAFION 115 polymer membrane.

Figure 12:
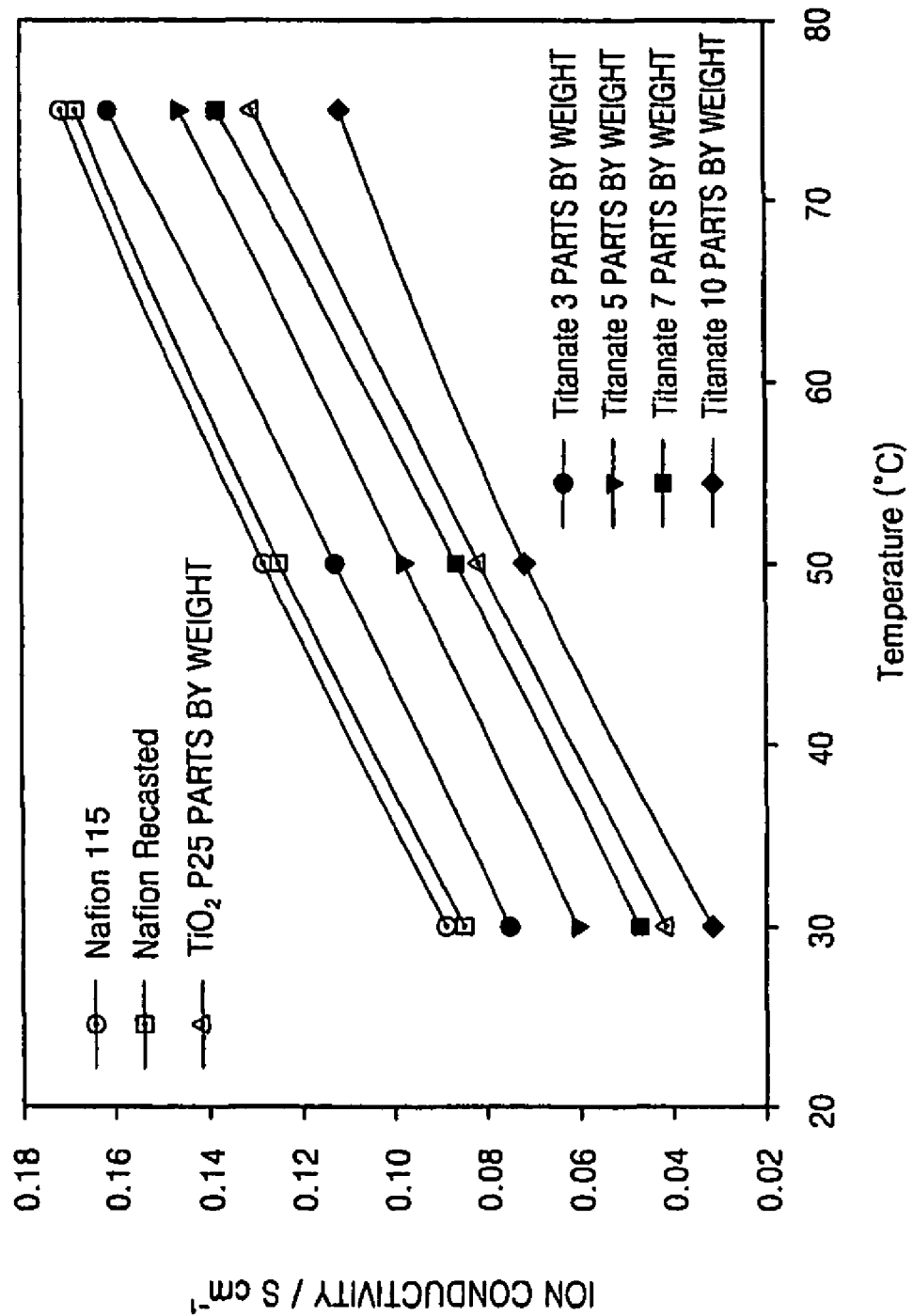
FIG. 12 is a graph illustrating the ion conductivities of the polymer nano-composite membranes of Examples 5-8, which are measured using a 4-point probe method.

The ion conductivity of the polymer nano-composite membranes prepared in Examples 5-8 was measured using a 4-point probe method and the results were shown in FIG. 12. In FIG. 12, NAFION 115 represents the ion conductivity of a commercially available NAFION 115 polymer membrane, NAFION Recasted represents the ion conductivity of a polymer membrane prepared in a similar method to Examples 5-8, and $TiO_2$ P25 represents the ion conductivity of a polymer membrane prepared using 3 parts by weight of $TiO_2$.

As apparent from FIG. 12, as the amount of the inorganic material increases, the proton conductivity decreases. Also, the polymer nano-composite membranes using 3 to 7 parts by weight of titanate have higher proton conductivity than the inorganic electrolyte membrane using $TiO_2$ P25. This is because a sulfonic acid group is introduced into the surface of titanate.

Figure 13:
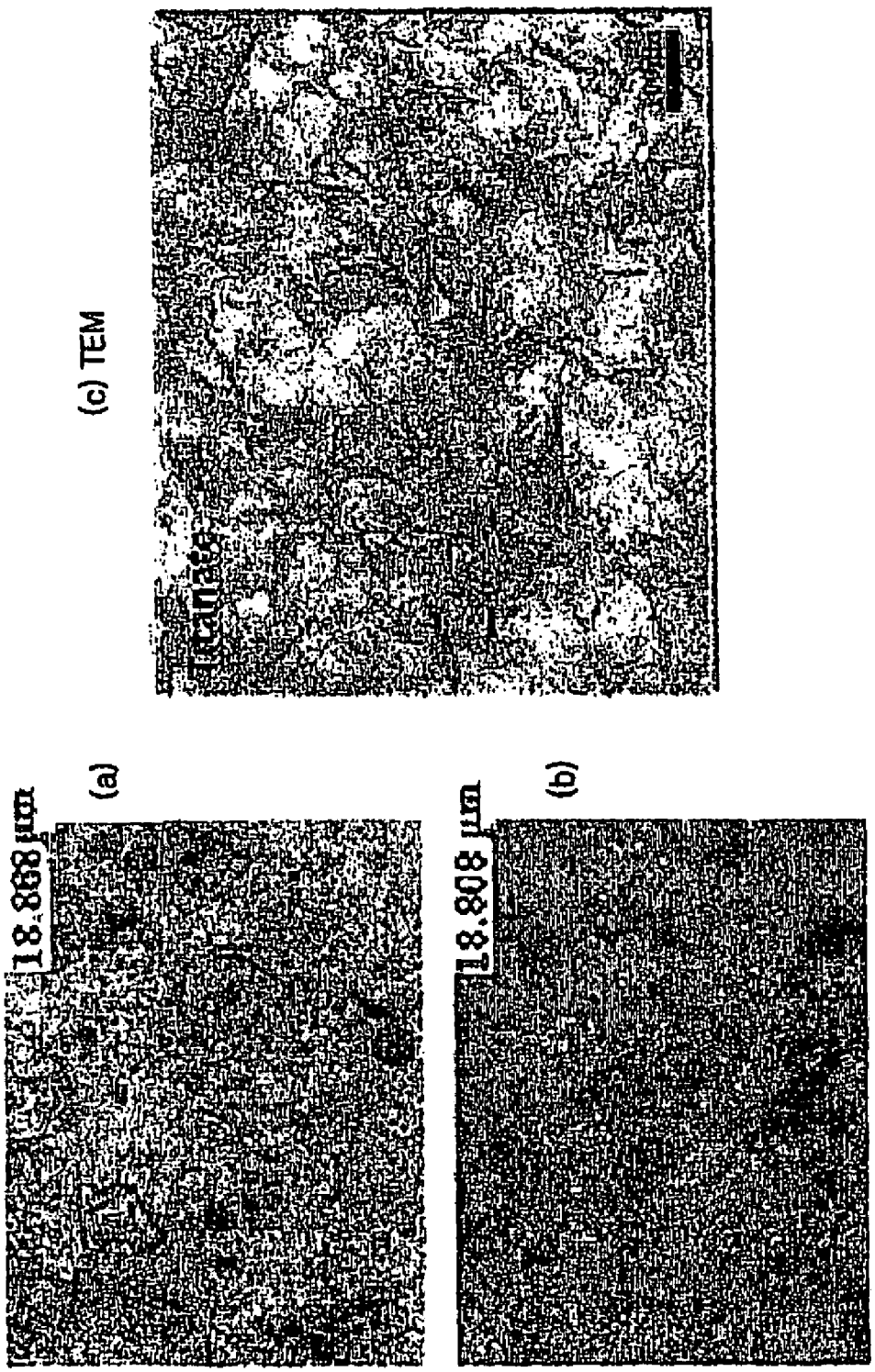
FIG. 13 is TEM images of the polymer nano-composite membrane used in Example 8.

The distribution state of the polymer nano-composite membrane used in Example 8 was investigated and the result is shown in FIG. 13. In FIG. 13, a and b are optical microscopic images and c is a TEM image.

From FIG. 13, the surface state and mixing state of the inorganic material-organic material composite membrane can be observed.

Figure 14:
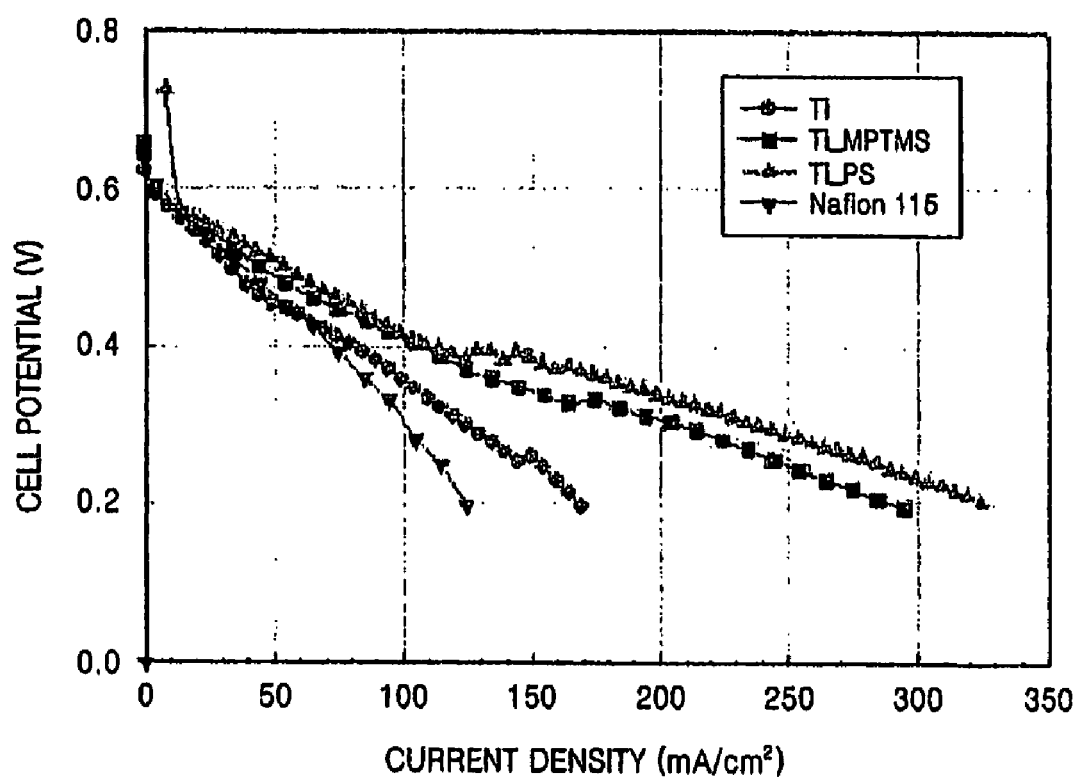
FIG. 14 is a graph showing the performance of a membrane and electrode assembly (MEA) using a polymer membrane including a proton conducting titanate of Preparation Example 2, an MEA using a membrane including Ti-MPTMS of Example 14, an MEA using a membrane including Ti—PS of Example 11, and an MEA using NAFION 115.

In addition, the performance of the MEAs prepared in Example 6 and Comparative Example 1 was investigated and the results are shown in FIG. 14. In FIG. 14, Ti represents the performance of the MEA using a membrane including $TiO_2$—P25, i.e., titanate having no sulfonic acid group introduced thereinto, Ti_MPTMS represents the performance of the MEA of Example 14, Ti_PS represents the performance of the MEA using the polymer membrane of Example 6, and NAFION 115 represents the performance of the MEA using a NAFION 115 polymer membrane.

Referring to FIG. 14, the performance of the MEA using the polymer membrane including the proton conducting titanate of Preparation Example 2, the MEAs using the membrane including Ti_MPTMS of Example 14 and the membrane including Ti_PS of Example 11, and the MEA using NAFION 115 can be confirmed.

It can be seen from FIG. 14 that a polymer composite membrane including an inorganic material having a high IEC value has also high MEA performance.

Figure 15:
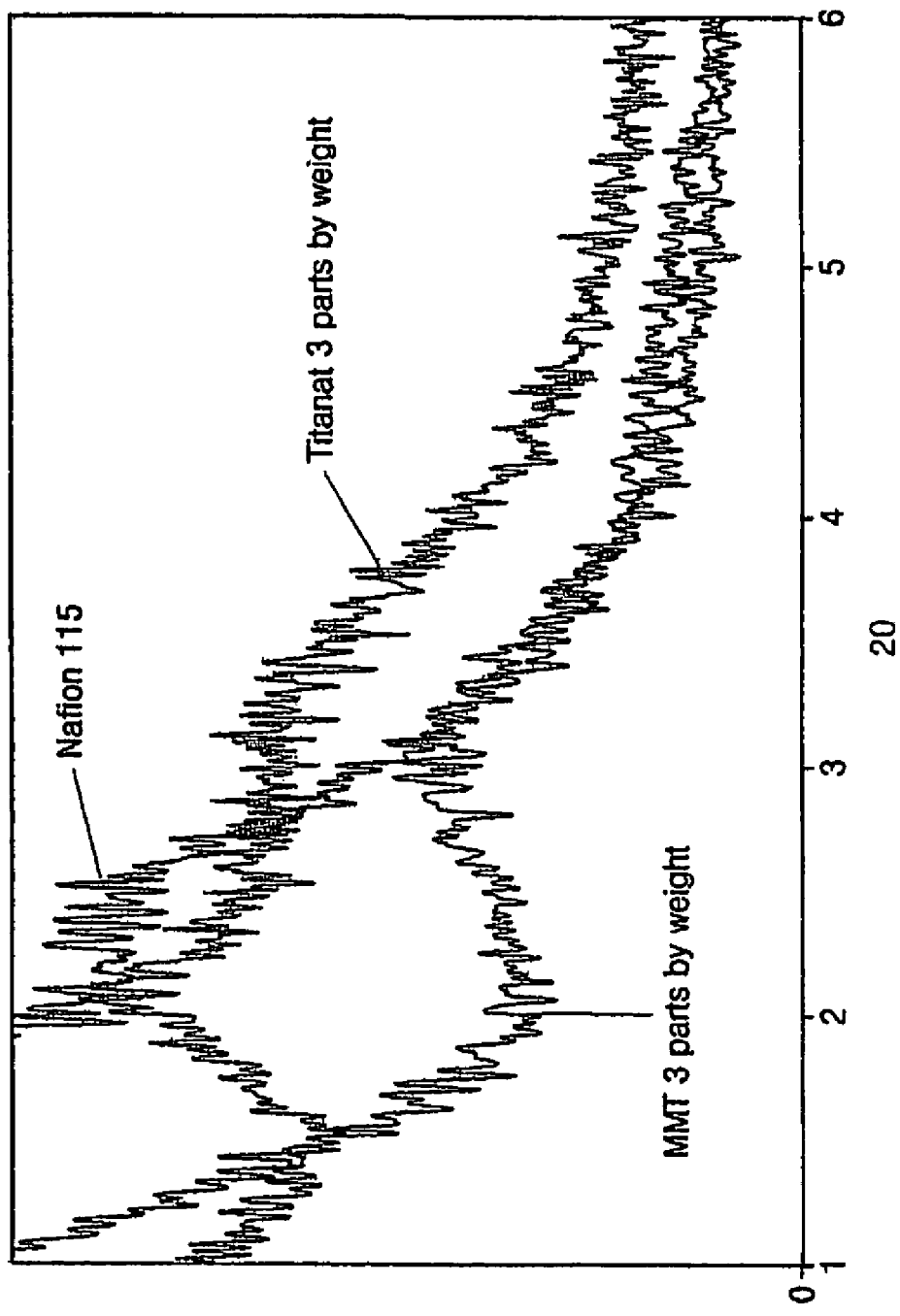
FIG. 15 is a graph showing X-ray diffraction (XRD) analysis results of a polymer nano-composite membrane used in Example 6 and polymer membrane used in Comparative Example 1.

The distribution state of the polymer nano-composite membrane used in Example 6 and Comparative Example 1 was investigated using XRD and the result is shown in FIG. 15. In FIG. 15, NAFION 115 represents a distribution state of a NAFION 115 polymer membrane, MMT 3 parts by weight represents a distribution state of the polymer membrane of Comparative Example 1 and Titanate 3 parts by weight represents a distribution state of the polymer nano-composite membrane of Example 6.

As is apparent from FIG. 15, interlayer materials are mixed, which is the characteristic of an inorganic material and the XRD peak shifts in a rightward direction.

The peak shift is due to a reduction in an ion channel size from 4 nm for NAFION to 3 nm for the inorganic material-organic material composite membrane.

The proton conducting titanate according to an embodiment of the present invention is provided with a sulfonic acid group-containing moiety having proton conductivity, which increases the proton conductivity of the polymer nano-composite membrane.

The polymer nano-composite membrane according to an embodiment of the present invention includes the proton conducting titanate, and thus can have a controllable degree of swelling in a methanol solution, and the transmittance of the polymer nano-composite membrane can be reduced. The polymer nano-composite membrane can be used as a proton conducting membrane in fuel cells to improve the thermal stability, energy density, and fuel efficiency of the fuel cells.

Although a few embodiments of the present invention have been shown and described, it would be appreciated by those skilled in the art that changes may be made in this embodiment without departing from the principles and spirit of the invention, the scope of which is defined in the claims and their equivalents.

What is claimed is:

1. A proton conducting titanate comprising:
   titanate of the formula $H_2Ti_3O_7$; and
   a sulfonic acid group-containing moiety having proton conductivity introduced into the surface of the titanate,
   wherein the sulfonic acid group-containing moiety is directly bound to the titanate via an ether bond (—O—) and wherein the sulfonic acid group-containing moiety is

wherein $R_1$ is a substituted or unsubstituted C1-C12 alkylene group or a substituted or unsubstituted C1-C12 alkenylene group, A is —C(R')(R")— or —C=O—, and R' and R" are each independently hydrogen or a C1-C10 alkyl group, or R' and R" together form a ring represented by the following formula:

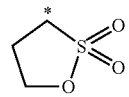

wherein * represents the position where R' and R" are attached to carbon; or

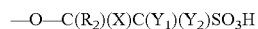

wherein $R_2$ is —F, —Cl, —SF$_5$, =SF$_4$, —SF$_4$Cl, —CF$_3$, —CF$_2$CF$_3$, —H(CF$_2$)$_4$, a C1-C12 alkyl group, a C1-C12 halogenated alkyl group, a C1-C12 alkenyl group, a C1-C12 halogenated alkenyl group, —CF$_2$OSO$_2$F, —(CF$_2$)$_4$CHFSO$_2$F, —CF$_2$CF$_2$CHFSO$_2$F, —CF$_2$CHFSO$_2$F, —CF$_2$OCF(CF$_3$)CF$_3$, —CF$_2$C(=CF$_2$)F, —CF$_2$OCF$_3$, —CF$_2$C(F)(Cl)CF$_2$CCl$_2$F, —CH$_2$CH(Cl)CH$_2$Cl, or a group represented by the following formula:

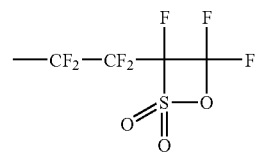

wherein X is —F, —H, —Cl or —CF$_3$, and $Y_1$ and $Y_2$ are each independently F or Cl.

2. The proton conducting titanate of claim 1, wherein the sulfonic acid group-containing moiety is:
   —O(CH$_2$)$_n$SO$_3$H wherein n is an integer from 1 to 13; or
   —O—C(R$_2$)(X)CF$_2$SO$_3$H wherein R$_2$ is —F, —CF$_3$, —SF$_5$, =SF$_4$, —SF$_4$Cl, —CF$_2$CF$_3$, or —H(CF$_2$)$_4$; and X is —F, —H, —Cl, or —CF$_3$.

3. The proton conducting titanate of claim 1, wherein the titanate has a morphology of a nanosheet, a nanofiber, or a mixture thereof.

4. A method of preparing the proton conducting titanate of claim 1, the method comprising sulfonating the titanate by reacting a sultone compound with the titanate in the presence of a solvent, wherein the sultone is selected to provide the sulfonic acid group-containing moiety when introduced to the surface of the titanate.

5. The method of claim 4, wherein the sultone compound is a compound represented by Formula 1 or a compound represented by Formula 2:

Formula 1

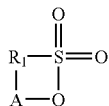

wherein R₁ is a substituted or unsubstituted C1-C12 alkylene group, or a substituted or unsubstituted C1-C12 alkenylene group, A is —C(R')(R")— or —C=O—, and R' and R" are each independently hydrogen or a C1-C10 alkyl group, or R' and R" together form a ring represented by the following formula:

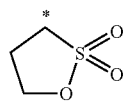

wherein * indicates the position where R' and R" are attached to carbon;

Formula 2

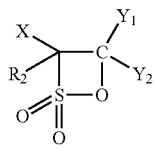

wherein R₂ is —F, —Cl, —SF₅, =SF₄, —SF₄Cl, —CF₃, —CF₂CF₃, —H(CF₂)₄, C1-C12 alkyl, C1-C12 halogenated alkyl, C1-C12 alkenyl, C1-C12 halogenated alkenyl, —CF₂OSO₂F, —(CF₂)₄CHFSO₂F, —CF₂CF₂CHFSO₂F, —CF₂CHFSO₂F, —CF₂OCF(CF₃)CF₃, —CF₂C(=CF₂)F, —CF₂OCF₃, —CF₂C(F)(Cl)CF₂CCl₂F, —CH₂CH(Cl)CH₂Cl, or a group represented by the following formula:

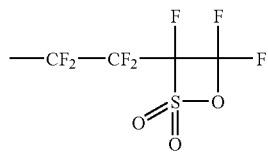

wherein X is —F, —H, —Cl or —CF₃, and Y₁ and Y₂ are each independently F or Cl.

6. The method of claim 4, wherein the sultone compound is selected from the group consisting of Compound (A) through Compound (S), which are represented by the following formulae:

(A)

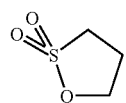

(B)

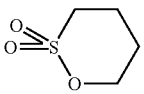

(C)

(D)

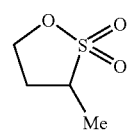

(E)

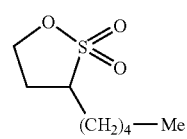

(F)

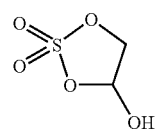

(G)

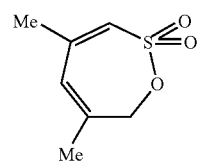

(H)

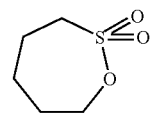

(I)

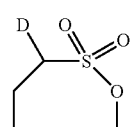

(J)

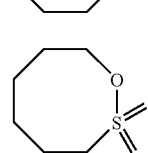

(K)

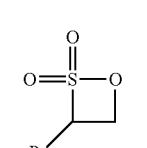

(L)

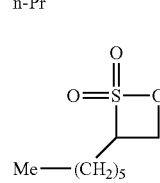

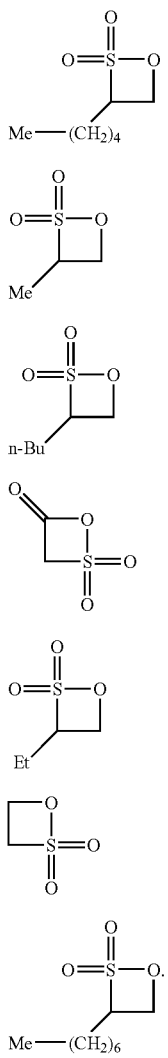
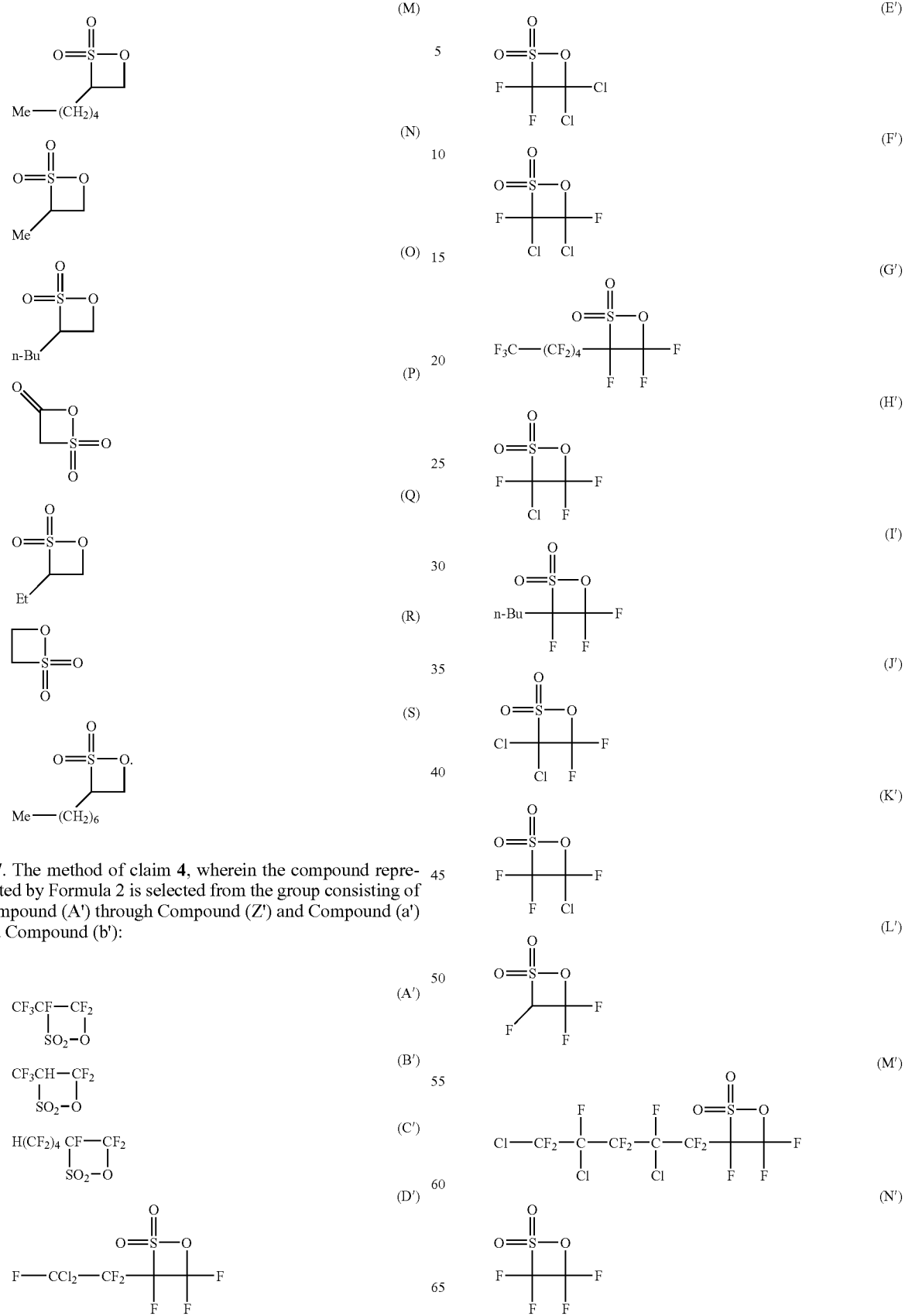
7. The method of claim 4, wherein the compound represented by Formula 2 is selected from the group consisting of Compound (A') through Compound (Z') and Compound (a') and Compound (b'):

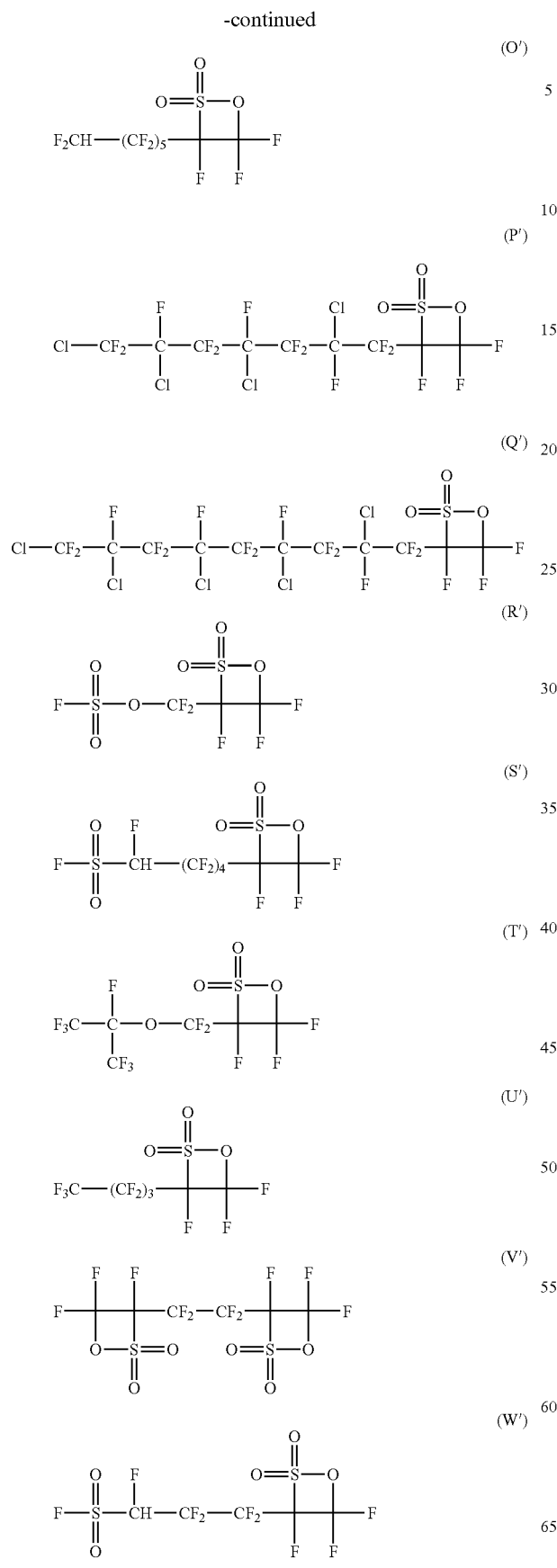

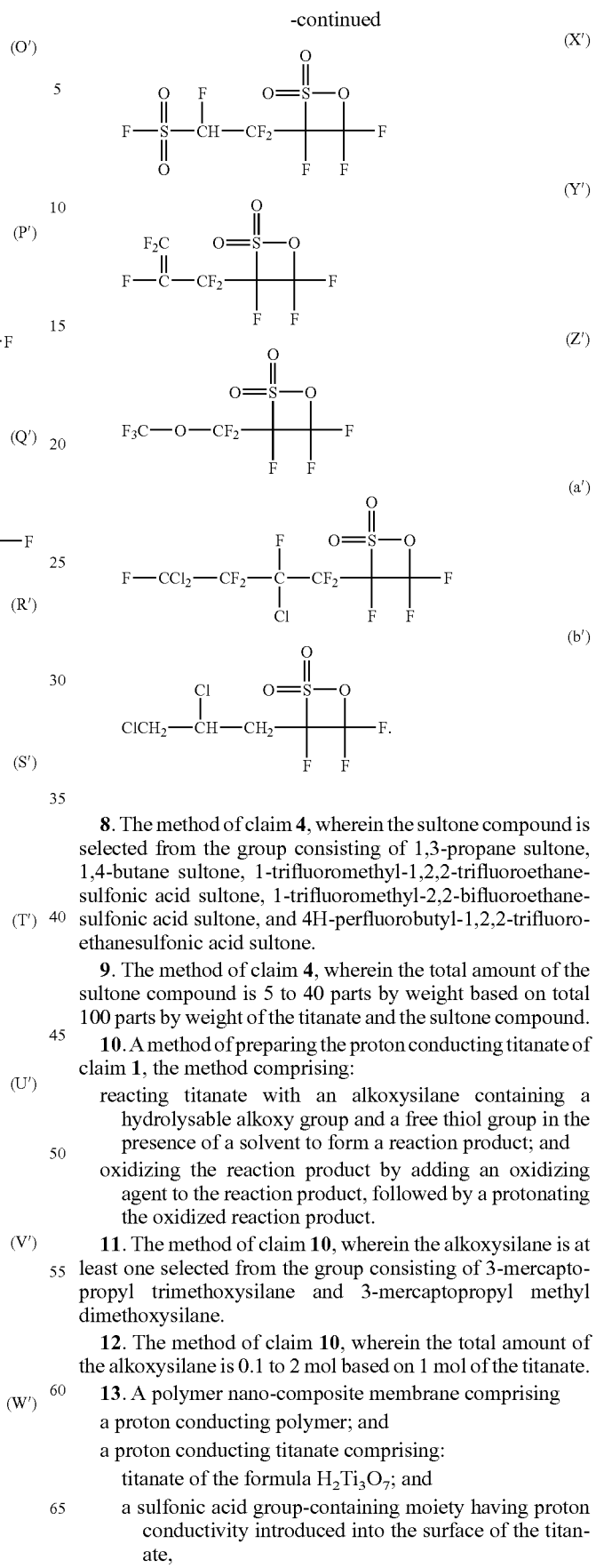

8. The method of claim 4, wherein the sultone compound is selected from the group consisting of 1,3-propane sultone, 1,4-butane sultone, 1-trifluoromethyl-1,2,2-trifluoroethanesulfonic acid sultone, 1-trifluoromethyl-2,2-bifluoroethanesulfonic acid sultone, and 4H-perfluorobutyl-1,2,2-trifluoroethanesulfonic acid sultone.

9. The method of claim 4, wherein the total amount of the sultone compound is 5 to 40 parts by weight based on total 100 parts by weight of the titanate and the sultone compound.

10. A method of preparing the proton conducting titanate of claim 1, the method comprising:
reacting titanate with an alkoxysilane containing a hydrolysable alkoxy group and a free thiol group in the presence of a solvent to form a reaction product; and
oxidizing the reaction product by adding an oxidizing agent to the reaction product, followed by a protonating the oxidized reaction product.

11. The method of claim 10, wherein the alkoxysilane is at least one selected from the group consisting of 3-mercaptopropyl trimethoxysilane and 3-mercaptopropyl methyl dimethoxysilane.

12. The method of claim 10, wherein the total amount of the alkoxysilane is 0.1 to 2 mol based on 1 mol of the titanate.

13. A polymer nano-composite membrane comprising
a proton conducting polymer; and
a proton conducting titanate comprising:
titanate of the formula $H_2Ti_3O_7$; and
a sulfonic acid group-containing moiety having proton conductivity introduced into the surface of the titanate, wherein the sulfonic acid group-containing moiety is directly bound to the titanate via an ether bond (—O—) and wherein the sulfonic acid group-containing moiety is

—O-AR₁SO₃H wherein R₁ is a substituted or unsubstituted C1-C12 alkylene group or a substituted or unsubstituted C1-C12 alkenylene group, A is —C(R')(R")— or —C=O—, and R' and R" are each independently hydrogen or a C1-C10 alkyl group, or R' and R" together form a ring represented by the following formula:

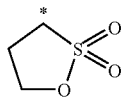

wherein * represents the position where R' and R" are attached to carbon; or

—O—C(R₂)(X)C(Y₁)(Y₂)SO₃H wherein R₂ is —F, —Cl, —SF₅, =SF₄, —SF₄Cl, —CF₃, —CF₂CF₃, —H(CF₂)₄, a C1-C12 alkyl group, a C1-C12 halogenated alkyl group, a C1-C12 alkenyl group, a C1-C12 halogenated alkenyl group, —CF₂OSO₂F, —(CF₂)₄CHFSO₂F, —CF₂CF₂CHFSO₂F, —CF₂CHFSO₂F, —CF₂OCF(CF₃)CF₃, —CF₂C(=CF₂)F, —CF₂OCF₃, —CF₂C(F)(Cl)CF₂CCl₂F, —CH₂CH(Cl)CH₂Cl, or a group represented by the following formula:

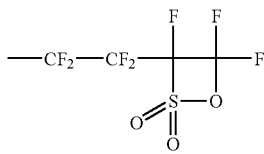

wherein X is —F, —H, —Cl or —CF₃, and Y₁ and Y₂ are each independently F or Cl.

14. The polymer nano-composite membrane of claim 13, wherein the sulfonic acid group-containing moiety is:
—O(CH₂)ₙSO₃H wherein n is an integer from 1 to 13; or
—O—C(R₂)(X)CF₂SO₃H wherein R₂ is —F, —CF₃, —SF₅, =SF₄, —SF₄Cl, —CF₂CF₃, or —H(CF₂)₄; and X is —F, —H, —Cl, or —CF₃).

15. The polymer nano-composite membrane of claim 13, wherein the proton conducting polymer includes at least one polymer selected from perfluorinated sulfonic acid polymers, sulfonated polyimides, sulfonated polyether ketones, sulfonated polystyrenes, and sulfonated polysulfones.

16. The polymer nano-composite membrane of claim 13, wherein the proton conducting polymer is contained in an amount of 400 to 3500 parts by weight based on 100 parts by weight of the proton conducting titanate.

17. The polymer nano-composite membrane of claim 13, wherein the proton conducting polymer is contained in an amount effective to reduce swelling of the membrane and to reduce transmittance of methanol through the membrane, in comparison to a membrane that contains only a proton conducting polymer.

18. The polymer nano-composite membrane of claim 13, wherein the thickness of the polymer nano-composite membrane is 20 to 200 μm.

19. A fuel cell comprising the polymer nano-composite membrane of claim 13.

20. A fuel cell comprising the polymer nano-composite membrane of claim 14.

21. A fuel cell comprising the polymer nano-composite membrane of claim 15.

22. A fuel cell comprising the polymer nano-composite membrane of claim 16.

23. A fuel cell comprising the polymer nano-composite membrane of claim 17.

24. The fuel cell of claim 18, wherein the cell is a direct methanol fuel cell.

25. The proton conducting titanate of claim 1, wherein the titanate has a morphology of a mixture of a nanosheet and a nanofiber, and wherein the mixing ratio of the nanosheet and nanofiber is in the range of 10:90 to 90:10.

* * * * *

UNITED STATES PATENT AND TRADEMARK OFFICE
CERTIFICATE OF CORRECTION

PATENT NO. : 7,842,199 B2
APPLICATION NO. : 11/438229
DATED : November 30, 2010
INVENTOR(S) : Hae-kyoung Kim et al.

It is certified that error appears in the above-identified patent and that said Letters Patent is hereby corrected as shown below:

Column 22, Claim 6, Formula (F), lines 25-29    Delete Formula "F" and Insert
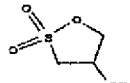
-- (F) --

Column 28, Claim 14, line 6    Delete "—$CF_3$)."
Insert -- —$CF_3$. --

Column 28, Claim 24, line 35    Delete "18"
Insert -- 19 --

Signed and Sealed this
Fourteenth Day of February, 2012

David J. Kappos
*Director of the United States Patent and Trademark Office*